United States Patent
Skerry et al.

(10) Patent No.: US 9,556,268 B2
(45) Date of Patent: *Jan. 31, 2017

(54) THERAPEUTIC AGENT

(71) Applicant: MEDELLA THERAPEUTICS LTD., Sheffield, South Yorkshire (GB)

(72) Inventors: Timothy Michael Skerry, Sheffield (GB); Gareth Owain Richards, Sheffield (GB)

(73) Assignee: Medella Therapeutics Ltd., Sheffield, South Yorkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/511,099

(22) Filed: Oct. 9, 2014

(65) Prior Publication Data

US 2015/0037344 A1 Feb. 5, 2015

Related U.S. Application Data

(60) Division of application No. 12/849,536, filed on Aug. 3, 2010, now Pat. No. 8,895,005, which is a continuation of application No. 12/090,635, filed as application No. PCT/GB2006/050338 on Oct. 18, 2006, now abandoned.

(30) Foreign Application Priority Data

Oct. 18, 2005 (GB) .................................. 0521139.6

(51) Int. Cl.
*A61K 39/395* (2006.01)
*C07K 16/28* (2006.01)

(52) U.S. Cl.
CPC ........... *C07K 16/28* (2013.01); *A61K 39/3955* (2013.01); *A61K 39/39558* (2013.01); *C07K 16/2869* (2013.01); *C07K 2317/56* (2013.01); *C07K 2317/569* (2013.01); *C07K 2317/76* (2013.01)

(58) Field of Classification Search
None
See application file for complete search history.

(56) References Cited

U.S. PATENT DOCUMENTS 8,389,237 B2 * 3/2013 Skerry ....................... 435/320.1
2006/0099622 A1 5/2006 Ni et al.

FOREIGN PATENT DOCUMENTS

WO 2004/050834 A2 6/2004
WO 2007/045927 A2 4/2007

OTHER PUBLICATIONS

Caldas, Cristina et al., "Humanization of the anti-CD18 antibody 6.7: an unexpected effect of framework residue in binding to antigen," Molecular Immunology, vol. 39, No. 15, pp. 941-952 (May 2003).

Campbell, Ailsa M., "Monoclonal Anitbody Technology: The Production and Characterization of Rodent and Human Hybridomas," Elsevier Science Publishers B.V., Amsterdam, The Nether lands, vol. 13, pp. 1-32 (1984).

Chauhan, M. et al, "Studies on the effects of the N-terminal domain antibodies of calcitonin receptor-like receptor and receptor activity-modifying protein 1 on calcitonin gene-related peptide-induced vasorelaxation in rat uterine artery." Biology of Reproduction, vol. 70, No. 6, pp. 1658-1663 (Jun. 2004).

Chien, Nadine C., et al., "Significant structural and functional change of an antigen-binding site by a distant amino acid substitution: Proposal of a structural mechanism," Proc. Natl. Acad. Sci. USA, vol. 86, No. 14, pp. 5532-5536 (Jul. 1989).

Conner, A.C. et al, "Heterodimers and family-B GPCRs: RAMPs, CGRP and adrenomedullin." Biochemical Society Transactions, vol. 32, Part 5, pp. 843-846 (Nov. 2004).

Cottrell, Graeme S. et al., "Localization of Calcitonin Receptor-Like Receptor and Receptor Activity Modifying Protein 1 in Enteric Neurons, Dorsal Root Ganglia, and the Spinal Cord of the Rat," The Journal of Comparative Neurology, vol. 490, No. 3, pp. 239-255 (Sep. 2005).

Fernandez-Sauze, Samantha et al, "Effects of adrenomedullin on endothelial cells in the multistep process of angiogenesis: Involvement of CRLR/RAMP2 and CRLR/RAMP3 receptors." International Journal of Cancer, vol. 108, No. 6, pp. 797-804 (Mar. 2004).

Fitzsimmons, Timothy J. et al, "The extracellular domain of receptor activity-modifying protein 1 is sufficient for calcitonin receptor-like receptor function." Journal of Biological Chemistry, vol. 278, No. 16, pp. 14313-14320 (Apr. 2003).

Giusti, Angela M. et al., "Somatic diversification of S107 from an antiphosphocholine to an anti-DFNA autoantibody is due to a single base change in its heavy chain variable region," Proc. Natl. Acad. Sci. USA, vol. 84, No. 9, pp. 2926-2930 (May 1987).

Gussow, Detlef et al., "Humanization of Monoclonal Antibodies," Methods in Enzymology, vol. 203, pp. 99-121 (1991).

Hay, D.L. et al, "CL/RAMP2 and CL/RAMP3 produce pharmacologically distinct adrenomedullin receptors: A comparison of effects of adrenomedullin22-52, CGRP8-37 and BIBN4096BS." British Journal of Pharmacology, vol. 140, No. 3, pp. 477-486 (Oct. 2003).

Ittner, Lars M. et al, "The N-terminal extracellular domain 23-60 of the calcitonin receptor-like receptor in chimeras with the parathyroid hormone receptor mediates association with receptor activity-modifying protein 1." Biochemistry, vol. 44, No. 15, pp. 5749-5754 (Apr. 2005).

Kato, J. et al, "Adrenomedullin: A possible autocrine or paracrine hormone in the cardiac ventricles." Hypertension Research, Osaka, JP, vol. 26, pp. S113-S119 (2003).

Keleg, Shereen et al., "Adrenomedullin is induced by hypoxia and enhances pancreatic cancer cell invasion," Int. J. Cancer, vol. 121, pp. 21-32 (2007).

Kuwasako, Kenji et al, "The seven amino acids of human RAMP2 (86-92) and RAMP3 (59-65) are critical for agonist binding to human adrenomedullin receptors." Journal of Biological Chemistry, vol. 276, No. 52, pp. 49459-49465 (Dec. 2001).

(Continued)

*Primary Examiner* — Marianne P Allen

(74) *Attorney, Agent, or Firm* — Senniger Powers LLP

(57) ABSTRACT

The present invention relates to agents which modulate the effect of a RAMP (Receptor Activity Modifying Protein) protein on a Calcitonin Receptor Like Receptor (CRLR). Also included in the present invention are methods and uses of such agents and assays for identifying such agents. The agents of the present disclosure may be used in the treatment of, for example, cancer, obesity and other disorders.

8 Claims, 20 Drawing Sheets

(56) References Cited

OTHER PUBLICATIONS

Mariuzza, R.A. et al., "Annual Review of Biophysics and Biophysical Chemistry," Annual Reviews, Palo Alto, CA, vol. 16, pp. 139-159 (1987).

Nowak, Wojciech et al., Novel regulation of adrenomedullin receptor by PDGF: role of receptor activity modifying protein-3, Am. J. Physiol. Cell Physiol., vol. 282, No. 6, pp. C1322-C1331 (Jan. 2002).

Ouafik, L'Houcine et al, "Neutralization of adrenomedullin inhibits the growth of human glioblastoma cell lines in vitro and suppresses tumor xenograft growth in vivo." American Journal of Pathology, vol. 160, No. 4, pp. 1279-1292 (Apr. 2002).

"Ramp Antibodies," Internet Article, http://ww.scbt.com/table.php?table=ramp, Santa Cruz Biotechnology, Inc. (2007).

Rudikoff, Stuart et al., "Single amino acid substitution altering antigen-binding specificity," Proc. Natl. Acad. Sci. USA, vol. 79, pp. 1979-1983 (Mar. 1982).

Winkler, Karsten et al., "changing the Antigen Binding Specificity by Single Point Mutations of an Anti-p24 (HIV-1) Antibody," J. Immunol., vol. 165, No. 8, pp. 4505-4514 (Oct. 2000).

Zudaire, E. et al, "Regulation of pancreatic physiology by adrenomedullin and its binding protein." Regulatory Peptides, vol. 112, No. 1-3, pp. 121-130 (Apr. 2003).

\* cited by examiner

Figure 1

DNA

CCAGCGGACT CGACTCGGCA CCGCTGTGCA CCATGGCCCG GGCCCTGTGC CGCCTCCCGC
GGCGCGGCCT CTGGCTGCTC CTGGCCCATC ACCTCTTCAT GACCACTGCC TGCCAGGAGG
CTAACTACGG TGCCCTCCTC CGGCAGCTCT GCCTCACCCA GTTCCAGGTA GACATGGAGG
CCGTCGGGGA GACGCTGTGG TGTGACTGGG GCAGGACCAT CAGGAGCTAC AGGGAGCTGG
CCGACTGCAC CTGGCACATG GCGGAGAAGC TGGGCTGCTT CTGGCCCAAT GCAGAGGTGG
CAGGTTCTT CCTGGCAGTG CATGGCCGCT ACTTCAGGAG CTGCCCCATC TCAGGCAGGG
CCGTGCGGGA CCCGCCCGGC AGCATCCTCT ACCCCTTCAT CGTGGTCCCC ATCACGGTGA
CCCTGCTGGT GACGGCACTG GTGGTCTGGC AGAGCAAGCG CACTGAGGGC ATTGTGTAGG
CGGGGCCCAG GCTGCCCGCG GGTGCACCCA GGCTGCAGGG TGAGGCCAGG CAGGCCTGGG
TAGGGGCAGC TTCTGGAGCC TTGGGACAGA GCAGGCCCAC AATGCCCCCC TTCTTCCAGC
CAAGAAGAGC TCACAGGACT CCAGAGTAGC CGAGGCTCTG GTATTAACCT GGAAGCCCCC
CTGGCTGCAG GCCACCGCCA CCCTAGGAAG GGGGCAGGGA CGTGACCTTG ACTTACCTCT
GGAAAGGGTC CCAGCCTAGA CTGCTTACCC CATAGCCACA TTTGTGGATG AGTGGTTTGT
GATTAAAAGG GATGTTCTTG

Protein

MAKALCRLPR RGLWLLLAHS LPMTTACQEA NYGALLRQLC LTQFQVDMEA VGETLWCDWG
RTIRSYRELA DCTWHMAEKL GCFWPNAEVD RFFLAVHGRY FRSCPISGRA VRDPPGSILY
PFIVVPITVT LLVTALVVWQ SKRTEGIV

Figure 2

DNA

```
GGATATAGGC GCCCCCACAC CCGGGCCCGG CTAAGCGCCG CCGCCGCTCC TCGCCTCCTT
GCTGCACGAT GGCCTCGCTC CGGGTGGAGC GCGCCGGCGG CCCGCGTCTC CCTAGGACCC
GAGTCGGGCG GCCGGCAGCC GTCCGCCTCC TCCTTCTGCT GGGCGCTGTC CTGAATCCCC
ACGAGGCCCT GGCTCAGCCT CTTCCCACCA CAGGCACACC AGGGTCAGAA GGGGGGACGG
TCAAGAACTA TGAGACAGCT GTCCAATTTT GCTGGAATCA TTATAAGGAT
CAAATGGATC CTATCGAAAA GGATTGGTGC GACTGGGCCA TGATTAGCAG GCCTTATAGC
ACCCTGCGAG ATTGCCTGGA GCACTTTGCA GAGTTGTTTG ACCTGGGCTT CCCCAATCCC
TTGGCAGAGA GGATCATCTT TGAGACTCAC CAGATCCACT TTGCCAACTG CTCCCTGGTG
CAGCCCACCT TCTCTGACCC CCCAGAGGAT GTACTCCTGG CCATGATCAT AGCCCCCATC
TGCCTCATCC CCTTCCTCAT CACTCTTGTA GTATGGAGGA GTAAAGACAG TGAGGCCCAG
GCCTAGGGGG CACGAGCTTC TCAACAACCA TGTTACTCCA CTTCCCCACC CCCACCAGGC
CTCCCTCCTC CCCTCCTACT CCCTTTTCTC ACTCTCATCC CCACCACAGA TCCCTGGATT
GCTGGAATG  GAAGCCAGGG  TTGGGCATGG  CACAAGTTCT  GTAATCTTCA
AAATAAAACT TTTTTTTTGA
```

Protein

```
MASLRVERAG GPRLPRTRVG RPAAVRLLLL LGAVLNPHEA LAQPLPTTGT PGSEGGTVKN
YETAVQFCWN HYKDQMDPIS KDWCDWAMIS RPYSTLRDCL EHFAELFDLG FPNPLAERII
FETHQIHFAN CSLVQPTFSD PPEDVLLAMI IAPICLIPFL ITLVVWRSKD SEAQA
```

Figure 3

DNA

```
GAGCGTGACC CAGCTGCGGC CGGCCAGCCA TGGAGACTGG AGCGCTGCGG CGCCCGCAAC
TTCTCCCGTT GCTGCTGCTG CTCTGCGGTG GGTGTCCCAG AGCAGGCGGC TGCAACGAGA
CAGGCATGTT GGAGAGGCTG CCCCTGTGTG GGAAGGCTTT CGCAGACATG ATGGGCAAGG
TGGACGTCTG GAAGTGGTGC AACCTGTCCG AGTTCATCGT GTACTATGAG AGTTTCACCA
ACTGCACCGA GATGGAGGCC AATGTCGTGG GCTGCTACTG GCCCAACCCC CTGGCCCAGG
GCTTCATCAC CGGCATCCAC AGCCAGTTCT TCTCCAACTG CACCGTGGAC AGGGTCCACT
TGGAGGACCC CCCAGACGAG GTTCTCATCC CGCTGATCGT TATACCCGTC GTTCTGACTG
TCGCCATGGC TGGCCTGGTG GTGTGGCGCA GCAAACGCAC CGACACGCTG CTGTCAGGGT
CCCGGTGAGA TGGAGTGGGT CACACCTGGC AAGCTGGAAG AAAGTTCCCT GGGGATGGGA
GATCGGGTGG GTGCTGCCAA TCTCAGCTA CTGTGGCCAC ACCCACCTG GTCATGGGCA
GACCCCTCCC TTCCTGGGCT GACCTGCTCC CTCGAGGCCA GCCTGCTCCC TGGCTGAGGC
TCAGGCTATC CGCCCAAGCT CTTTGCTCAT TCTAGGGCCA GTGGAGGAAA ATGTGATAAG
GCCAGAGCTT GTGTGCTGGG CAAGAAATCA CCTGCTGCAT CCTGTGCTCC GCAGGCTGGG
CCGGAAGCCT CTGCCTGCAG GTTCTATGC TGTTTCTTAG CACAGAATCC AGCCTAGCCT
TAGCCGCAGT CTAGGCCCTG CTTGGACTAG GACTCCTTGC TTGACCCCAT CTCTGGTTCC
TGCCCTGGCT CCTGCACCAG CCCCAGCTCC TGCCTACATC CAGGCAGAAA TATAGGCAGG
GGCTCTTGGA AGACGTTCCG TGCTGTGACC TCCGAGCCCT CCTGGTGGGA AGACAGCTGG
AAAGGCTGGG AGGAGAAGGG AGGGGCTGGG GGTTCCCAGG AGCCATGCGT GGCCTGCAGA
GTCCATTCCA TCATGATGCT GTGCCCGCTA TGGGCTGTGT CCATGACCAG AGGCTGGAGT
GGGGGTGTGT TATAGCCCCT CACCGGGACT TGCTGTGCGG ATGGGGCCTG GGCCTCCTTC
CTACAGGGGC TCCTCTGTGG GTGAGGGGCC CTCTGGAATG GCATCCCATG AGCTTGTGGC
CTCTATCTGC TACCATCTGT GTTTTATCTG AGTAAAGTTA CCTTACTTCT GG
```

Protein

```
METGALRRPQ LLPLLLLLCG GCPRAGGCNE TGMLERLPLC GKAFADMMGK VDVWKWCNLS
EFIVYYESFT NCTEMEANVV GCYWPNPLAQ GFITGIHRQF FSNCTVDRVH LEDPPDEVLI
PLIVIPVVLT VAMAGLVVWR SKRTDTLL
```

Figure 4

RAMP1

DNA

CTGCC TGCCAGGAGG CTAACTACGG TGCCCTCCTC CGGGAGCTCT GCCTCACCCA
GTTCCAGGTA GACATGGAGG CCGTCGGGGA GACGCTGTGG TGTGACTGGG GCAGGACCAT
CAGGAGCTAC AGGGAGCTGG CCGACTGCAC CTGGCACATG GCGGAGAAGC TGGCCTGCTT
CTGGCCCAAT GCAGAGGTGG CAGGTTCTT CCTGGCAGTG CATGGCCGCT ACTTCAGGAG
CTGCCCCATC TCAGGCAGGG CCGTGCGGGA CCCGCCCGGC AGCAT

Protein

ACQEA NYGALLRELC LTQFQVDMEA VGETLWCDWG RTIRSYRELA DCTWHMAEKL
GCFWPNAEVD RFFLAVHGRY FRSCPISGRA VRDPPGSI

Figure 5

RAMP2

DNA

AATCCCC ACGAGGCCCT GGCTCAGCCT CTTCCCACCA CAGGCACACC AGGGTCAGAA
GGGGGGACGG TGAAGAACTA TGAGACAGCT GTCCAATTTT GCTGGAATCA
TTATAAGGAT CAAATGGATC CTATCGAAAA GGATTGGTGC GACTGGGCCA TGATTAGCAG
GCCTTATAGC ACCCTGCGAG ATTGCCTGGA GCACTTTGCA GAGTTGTTTG ACCTGGGCTT
CCCCAATCCC TTGGCAGAGA GGATCATCTT TGAGACTCAC CAGATCCACT TTGCCAACTG
CTCCCTGGTG CAGCCCACCT TCTCTGACCC CCAGAGGAT GTA

Protein

LCAVLNPHEA LAQPLPTTGT PGSEGGTVKN YETAVQFCWN HYKDQMDPIE KDWCDWAMIS
RPYSTLRDCL EHFAELFDLG FPNPLAERII FETHQIHFAN CSLVQPTFSD PPRDVL

Figure 6

RAMP3

DNA
CAG AGCAGGCGGC TGCAACGAGA CAGGCATGTT GGAGAGGCTG CCCCTGTGTG
GGAAGGCTTT CGCAGACATG ATGGGCAAGG TGGACGTCTG GAAGTGGTGC AACCTGTCCG
AGTTCATCGT GTACTATGAG AGTTTCACCA ACTGCACCGA GATGGAGGCC AATGTCGTGG
GCTGCTACTG GCCCAACCCC CTGGCCCAGG GCTTCATCAC CGGCATCCAC AGGCAGTTCT
TCTCCAACTG CACCGTGGAC AGGGTCCACT TGGAGGACCC CCCAGACGAG GTTCTCATCC
CGCTGATCGT TATACCCGTC GTTCTGACTG TCGCCATGGC TGGCCTGGTG GTG

Protein
GCPRAGGCNE TGMLERLPLC GKAFADMMGK VDVWKWCNLS EFIVYYESFT NCTEMEANVV
GCYWPNPLAQ GFITGIHRQF FSNCTVDRVH LEDPPDEV

Figure 7A
1-50

DNA
CTGCC TGCCAGGAGG CTAACTACGG TGCCCTCCTCCGGGAGCTCT
GCCTCACCCAGTTCCAGGTAGACATGGAGGCCGTCGGGGAGACGCTGTGG
TGTGACTGGG GCAGGACCAT CAGGAGCTACAGGGAGCTGG
CCGACTGCACCTGGC

Protein
ACQEANYGALLRELCLTQFQVDMEAVGETLWCDWGRTIRSYRELADCTWH

Figure 7B
1-30

DNA
CTGCC TGCCAGGAGG CTAACTACGG TGCCCTCCTC CGGGAGCTCT
GCCTCACCCA GTTCCAGGTA GACATGGAGG CCGTCGGGGA GACGC

Protein
ACQEANYGALLRELCLTQFQVDMEAVGETL

Figure 7C
1-20

DNA
CTGCC TGCCAGGAGG CTAACTACGG TGCCCTCCTC CGGGAGCTCT
GCCTCACCCA GTTCC

Protein
ACQEANYGALLRELCLTQFQ

Figure 7D
10-50

DNA
CCCTCCTC CGGGAGCTCT GCCTCACCCA GTTCCAGGTA GACATGGAGG
CCGTCGGGGA GACGCTGTGG TGTGACTGGG GCAGGACCAT CAGGAGCTAC
AGGGAGCTGG CCGACTGCAC CTGGC

Protein
LRELCLTQFQVDMEAVGETLWCDWGRTIRSYRELADCTWH

Figure 7E
20-50

DNA
TCCAGGTA GACATGGAGG CCGTCGGGGA GACGCTGTGG TGTGACTGGG
GCAGGACCAT CAGGAGCTAC AGGGAGCTGG CCGACTGCAC CTGGC

Protein
MEA VGETLWCDWG RTIRSYRELA DCTWHM

Figure 7F
30-90

DNA
CGCTGTGG TGTGACTGGG GCAGGACCAT CAGGAGCTAC AGGGAGCTGG
CCGACTGCAC CTGGCACATG GCGGAGAAGC TGGGCTGCTT CTGGCCCAAT
GCAGAGGTGG CAGGTTCTT CCTGGCAGTG CATGGCCGCT ACTTCAGGAG
CTGCCCCATC TCAGGCAGGG CCGTGCGGGA CCCGCCCGGC AG

Protein
VGETLWCDWG RTIRSYRELA DCTWHMAEKL GCFWPNAEVD RFFLAVHGRY
FRSCPISGRA VRDPP

Figure 7G
40-80

DNA
GGAGCTAC AGGGAGCTGG CCGACTGCAC CTGGCACATG GCGGAGAAGC
TGGGCTGCTT CTGGCCCAAT GCAGAGGTGG CAGGTTCTT CCTGGCAGTG
CATGGCCGCT ACTTCAGGAG CTGCCCC

Protein
RTIRSYRELA DCTWHMAEKL GCFWPNAEVD RFFLAVHGRY FRSCP

Figure 7H
50-93

DNA
GGCACATG GCGGAGAAGC TGGGCTGCTT CTGGCCCAAT GCAGAGGTGG
CAGGTTCTT CCTGGCAGTG CATGGCCGCT ACTTCAGGAG CTGCCCCATC
TCAGGCAGGG CCGTGCGGGA CCCGCCCGGC AGCAT

Protein
AEKL GCFWPNAEVD RFFLAVHGRY FRSCPISGRA VRDPPGSI

Figure 8A
1-50
DNA
AATCCCC ACGAGGCCCT GGCTCAGCCT CTTCCCACCA CAGGCACACC
AGGGTCAGAA GGGGGGACGG TGAAGAACTA TGAGACAGCT GTCCAATTTT
GCTGGAATCA TTATAAGGAT CAAATGGATC CTATCGAAAA GGATTGGTGC
GAC Protein
LGAVLNPHEA LAQPLPTTGT PGSEGGTVKN YETAVQFCWN HYKDQMDPIE Figure 8B
1-30
DNA
AATCCCC ACGAGGCCCT GGCTCAGCCT CTTCCCACCA CAGGCACACC
AGGGTCAGAA GGGGGGACGG TGAAGAACTA TGAGACAGCT GTC Protein
LGAVLNPHEA LAQPLPTTGT PGSEGGTVKN Figure 8C
1-20
DNA
AATCCCC ACGAGGCCCT GGCTCAGCCT CTTCCCACCA CAGGCACACC
AGGGTCAGAA GGG Protein
LGAVLNPHEA LAQPLPTTGT Figure 8D
10-50
DNA
CTTCCCACCA CAGGCACACC AGGGTCAGAA GGGGGGACGG TGAAGAACTA
TGAGACAGCT GTCCAATTTT GCTGGAATCA TTATAAGGAT CAAATGGATC
CTATCGAAAA GGATTGGTGC GAC Protein
LAQPLPTTGT PGSEGGTVKN YETAVQFCWN HYKDQMDPIE

Figure 8E
20-50
Protein
PGSEGGTVKN YETAVQFCWN HYKDQMDPIE

Figure 8F
30-100
DNA
GTCCAATTTT GCTGGAATCA TTATAAGGAT CAAATGGATC CTATCGAAAA
GGATTGGTGC GACTGGGCCA TGATTAGCAG GCCTTATAGC ACCCTGCGAG
ATTGCCTGGA GCACTTTGCA GAGTTGTTTG ACCTGGGCTT CCCCAATCCC
TTGGCAGAGA GGATCATCTT TGAGACTCAC CAGATCCACT TTGCCAACTG
CTCCCTGGTG CAGC Protein
YETAVQFCWN HYKDQMDPIE KDWCDWAMIS RPYSTLRDCL EHFAELFDLG
FPNPLAERII FETHQIHFAN

Figure 8G
40-100
DNA
CAAATGGATC CTATCGAAAA GGATTGGTGC GACTGGGCCA TGATTAGCAG
GCCTTATAGC ACCCTGCGAG ATTGCCTGGA GCACTTTGCA GAGTTGTTTG
ACCTGGGCTT CCCCAATCCC TTGGCAGAGA GGATCATCTT TGAGACTCAC
CAGATCCACT TTGCCAACTG CTCCCTGGTG CAGC Protein
HYKDQMDPIE KDWCDWAMIS RPYSTLRDCL EHFAELFDLG FPNPLAERII
FETHQIHFAN

Figure 8H
50-100
DNA
GACTGGGCCA TGATTAGCAG GCCTTATAGC ACCCTGCGAG ATTGCCTGGA
GCACTTTGCA GAGTTGTTTG ACCTGGGCTT CCCCAATCCC TTGGCAGAGA
GGATCATCTT TGAGACTCAC CAGATCCACT TTGCCAACTG CTCCCTGGTG
CAGC Protein
KDWCDWAMIS RPYSTLRDCL EHFAELFDLG FPNPLAERII FETHQIHFAN
CSLVQPTFSD

DNA
ACCCTGCGAG ATTGCCTGGA GCACTTTGCA GAGTTGTTTG ACCTGGGCTT
CCCCAATCCC TTGGCAGAGA GGATCATCTT TGAGACTCAC CAGATCCACT
TTGCCAACTG CTCCCTGGTG CAGC

Protein
RPYSTLRDCL EHFAELFDLG FPNPLAERII FETHQIHFAN CSLVQPTFSD

DNA
GAGTTGTTTG ACCTGGGCTT CCCCAATCCC TTGGCAGAGA GGATCATCTT
TGAGACTCAC CAGATCCACT TTGCCAACTG CTCCCTGGTG CAGC

Protein
EHFAELFDLG FPNPLAERII FETHQIHFAN

Figure 9A 1-50
DNA
CAG AGCAGGCGGC TGCAACGAGA CAGGCATGTT GGAGAGGCTG
CCCCTGTGTG GGAAGGCTTT CGCAGACATG ATGGGCAAGG TGGACGTCTG
GAAGTGGTGC AACCTGTCCG AGTTCATCGT GTACTATGAG AGTTTCACCA
ACTGCAC Protein
GCPRAGGCNE TGMLERLPLC GKAFADMMGK VDVWKWCNLS EFIVYYESFT

Figure 9B 1-40
DNA
CAG AGCAGGCGGC TGCAACGAGA CAGGCATGTT GGAGAGGCTG
CCCCTGTGTG GGAAGGCTTT CGCAGACATG ATGGGCAAGG TGGACGTCTG
GAAGTGGTGC AACCTGTCCG AGTTCAT Protein
GCPRAGGCNE TGMLERLPLC GKAFADMMGK VDVWKWCNLS

Figure 9C 1-30
DNA
CAG AGCAGGCGGC TGCAACGAGA CAGGCATGTT GGAGAGGCTG
CCCCTGTGTG GGAAGGCTTT CGCAGACATG ATGGGCAAGG TGGACGT Protein
GCPRAGGCNE TGMLERLPLC GKAFADMMGK

Figure 9D 40-60
DNA
CATCGT GTACTATGAG AGTTTCACCA ACTGCACCGA GATGGAGGCC
AATGTCGTGG GCTGCTA Protein
EFIVYYESFT NCTEMEANVV

CACCGA GATGGAGGCC AATGTCGTGG GCTGCTACTG GCCCAACCCC
CTGGCCCAGG GCTTCAT

Protein
NCTEMEANVV GCYWPNPLAQ

Figure 9F

50-80
DNA
CACCGA GATGGAGGCC AATGTCGTGG GCTGCTACTG GCCCAACCCC
CTGGCCCAGG GCTTCATCAC CGGCATCCAC AGGCAGTT

Protein
NCTEMEANVV GCYWPNPLAQ GFITGIHRQF

Figure 9G

50-90
DNA

CACCGA GATGGAGGCC AATGTCGTGG GCTGCTACTG GCCCAACCCC
CTGGCCCAGG GCTTCATCAC CGGCATCCAC AGGCAGTTCT TCTCCAACTG
CACCGTGGAC AGGGTCCA

Protein
NCTEMEANVV GCYWPNPLAQ GFITGIHRQF FSNCTVDRVH

Figure 9H

50-93
DNA
CACCGA GATGGAGGCC AATGTCGTGG GCTGCTACTG GCCCAACCCC
CTGGCCCAGG GCTTCATCAC CGGCATCCAC AGGCAGTTCT TCTCCAACTG
CACCGTGGAC AGGGTCCACT TGGAGGACCC CCCAGACGAG GTTCTCATCC
CGCTGATCGT TATACCCGTC GTTCTGACTG TCGCCATGGC TGGCCTGGTC
GTG

Protein
NCTEMEANVV GCYWPNPLAQ GFITGIHRQF FSNCTVDRVH LEDPPDEV

Figure 10

SEQUENCE LISTING

```
<160> NUMBER OF SEQ ID NOS: 84

<210> SEQ ID NO 1
<211> LENGTH: 799
<212> TYPE: DNA
<213> ORGANISM: Homo sapiens

<400> SEQUENCE: 1
cgagcggact cgactcggca ccgctgtgca ccatggcccg ggccctgtgc cgcctcccgc      60
ggcgcggcct ctggctgctc ctggcccatc acctcttcat gaccactgcc tgccaggagg     120
ctaactacgg tgccctcctc cgggagctct gcctcaccca gttccaggta gacatggagg     180
ccgtcgggga gacgctgtgg tgtgactggg gcaggaccat caggagctac agggagctgg     240
ccgactgcac ctggcacatg gcggagaagc tgggctgctt ctggcccaat gcagaggtgg     300
caggttcttc ctggcagtgc atggccgcta cttcaggagc tgccccatct caggcagggc     360
cgtgcgggac ccgcccggca gcatcctcta ccccttcatc gtggtcccca tcacggtgac     420
cctgctggtg acggcactgg tggtctggca gagcaagcgc actgagggca ttgtgtaggc     480
ggggcccagg ctgcccgcgg gtgcacccag gctgcagggt gaggccaggc aggcctgggt     540
aggggcagct tctggagcct tgggacagag caggcccaca atgccccct tcttccagcc     600 aagaagagct cacaggagtc cagagtagcc gaggctctgg tattaacctg gaagcccccc     660
tggctggagg ccaccgccac cctaggaagg gggcagggac gtgaccttga cttacctctg     720
gaaagggtcc cagcctagac tgcttacccc atagccacat ttgtggatga gtggtttgtg     780 attaaaggg atgttcttg                                                   799

<210> SEQ ID NO 2
<211> LENGTH: 148
<212> TYPE: PRT
<213> ORGANISM: Homo Sapiens

<400> SEQUENCE: 2

Met Ala Arg Ala Leu Cys Arg Leu Pro Arg Arg Gly Leu Trp Leu Leu
  1               5                  10                  15

Leu Ala His His Leu Phe Met Thr Thr Ala Cys Gln Glu Ala Asn Tyr
                 20                  25                  30

Gly Ala Leu Leu Arg Glu Leu Cys Leu Thr Gln Phe Gln Val Asp Met
             35                  40                  45
```

Glu Ala Val Gly Glu Thr Leu Trp Cys Asp Trp Gly Arg Thr Ile Arg
        50                  55                  60

Ser Tyr Arg Glu Leu Ala Asp Cys Thr Trp His Met Ala Glu Lys Leu
65                  70                  75                  80

Gly Cys Phe Trp Pro Asn Ala Glu Val Asp Arg Phe Phe Leu Ala Val
                85                  90                  95

His Gly Arg Tyr Phe Arg Ser Cys Pro Ile Ser Gly Arg Ala Val Arg
            100                 105                 110

Asp Pro Pro Gly Ser Ile Leu Tyr Pro Phe Ile Val Val Pro Ile Thr
            115                 120                 125

Val Thr Leu Leu Val Thr Ala Leu Val Val Trp Gln Ser Lys Arg Thr
            130                 135                 140

Glu Gly Ile Val
145

<210> SEQ ID NO 3
<211> LENGTH: 780
<212> TYPE: DNA
<213> ORGANISM: Homo Sapiens

<400> SEQUENCE: 3
ggatataggc gcccccacac ccgggcccgg ctaagcgccg ccgccgctcc tcgcctcctt      60
gctgcacgat ggcctcgctc cgggtggagc gcgccggcgg cccgcgtctc cctaggaccc     120
gagtcgggcg gccggcagcc gtccgcctcc tccttctgct gggcgctgtc ctgaatcccc     180
acgaggccct ggctcagcct cttcccacca caggcacacc agggtcagaa gggggggacgg    240 tgaagaacta tgagacagct gtccaatttt gctggaatca ttataaggat caaatggatc     300
ctatcgaaaa ggattggtgc gactgggcca tgattagcag gccttatagc accctgcgag     360
attgcctgga gcactttgca gagttgtttg acctgggctt ccccaatccc ttggcagaga     420
ggatcatctt tgagactcac cagatccact ttgccaactg ctccctggtg cagcccacct     480
tctctgaccc cccagaggat gtactcctgg ccatgatcat agcccccatc tgcctcatcc     540
ccttcctcat cactcttgta gtatggagga gtaaagacag tgaggcccag gcctaggggg    600
cacgagcttc tcaacaacca tgttactcca cttccccacc cccaccaggc ctccctcctc     660
ccctcctact ccctttttctc actctcatcc ccaccacaga tccctggatt gctgggaatg   720
gaagccaggg ttgggcatgg cacaagttct gtaatcttca aaataaaact tttttttttga   780

<210> SEQ ID NO 4
<211> LENGTH: 175
<212> TYPE: PRT
<213> ORGANISM: Homo Sapiens

<400> SEQUENCE: 4

Met Ala Ser Leu Arg Val Glu Arg Ala Gly Gly Pro Arg Leu Pro Arg
1               5                   10                  15

Thr Arg Val Gly Arg Pro Ala Ala Val Arg Leu Leu Leu Leu Leu Gly
            20                  25                  30

Ala Val Leu Asn Pro His Glu Ala Leu Ala Gln Pro Leu Pro Thr Thr
        35                  40                  45

Gly Thr Pro Gly Ser Glu Gly Gly Thr Val Lys Asn Tyr Glu Thr Ala
        50                  55                  60

Val Gln Phe Cys Trp Asn His Tyr Lys Asp Gln Met Asp Pro Ile Glu
65                  70                  75                  80

```
Lys Asp Trp Cys Asp Trp Ala Met Ile Ser Arg Pro Tyr Ser Thr Leu
                85                  90                  95

Arg Asp Cys Leu Glu His Phe Ala Glu Leu Phe Asp Leu Gly Phe Pro
            100                 105                 110

Asn Pro Leu Ala Glu Arg Ile Ile Phe Glu Thr His Gln Ile His Phe
        115                 120                 125

Ala Asn Cys Ser Leu Val Gln Pro Thr Phe Ser Asp Pro Pro Glu Asp
    130                 135                 140

Val Leu Leu Ala Met Ile Ile Ala Pro Ile Cys Leu Ile Pro Phe Leu
145                 150                 155                 160

Ile Thr Leu Val Val Trp Arg Ser Lys Asp Ser Glu Ala Gln Ala
                165                 170                 175

<210> SEQ ID NO 5
<211> LENGTH: 1312
<212> TYPE: DNA
<213> ORGANISM: Homo sapiens

<400> SEQUENCE: 5
gagcgtgacc cagctgcggc cggccagcca tggagactgg agcgctgcgg cgcccgcaac      60
ttctcccgtt gctgctgctg ctctgcggtg ggtgtcccag agcaggcggc tgcaacgaga     120
caggcatgtt ggagaggctg cccctgtgtg ggaaggcttt cgcagacatg atgggcaagg     180
tggacgtctg gaagtggtgc aacctgtccg agttcatcgt gtactatgag agtttccacca    240 actgcaccga gatggaggcc aatgtcgtgg gctgctactg gcccaacccc ctggcccagg     300
gcttcatcac cggcatccac aggcagttct tctccaactg caccgtggac agggtccact     360
tggaggaccc cccagacgag gttctcatcc cgctgatcgt tatacccgtc gttctgactg     420
tcgccatggc tggcctggtg gtgtggcgca gcaaacgcac cgacacgctg ctgtgagggt     480
cccggtgaga tggagtgggt cacacctggc aagctggaag aaagttccct ggggatggga     540
gatcgggtgg gtgctgccaa tctccagcta ctgtggccac accccacctg gtcatgggca     600
gaccctcccc ttcctgggct gacctgctcc tcgaggcca gcctgctccc tggctgaggc      660
tcaggctatc cgcccaagct cttcgctcat tctaggccct gtggaggaaa atgtgataag     720
gccagagctt gtgtgctggg caagaaatca cctgctgcat cctgtgctcc gcaggctggg     780
ccggaagcct ctgcctgcag gtttctatgc tgtttcttag cacagaatcc agcctagcct     840
tagccgcagt ctaggccctg cttggactag gactccttgc ttgaccccat ctctggttcc     900
tgccctggct cctgcaccag ccccagctcc tgcctacatc caggcagaaa tataggcagg     960
ggctcttgga agacgttccg tgctgtgacc tccgagccct cctggtggga agacagctgg    1020
aaaggctggg aggagaaggg aggggctggg ggttcccagg agccatgcgt ggcctgcaga    1080
gtccattcca tcatgatgct gtgcccgcta tgggctgtgt ccatgaccag aggctggagt    1140
gggggtgtgt tatagcccct caccgggact tgctgtgcgg atggggcctg ggcctccttc    1200
ctacaggggc tcctctgtgg gtgaggggcc ctctggaatg gcatcccatg agcttgtggc    1260
ctctatctgc taccatctgt gttttatctg agtaaagtta ccttacttct gg            1312

<210> SEQ ID NO 6
<211> LENGTH: 148
<212> TYPE: PRT
<213> ORGANISM: Homo Sapiens

<400> SEQUENCE: 6

Met Glu Thr Gly Ala Leu Arg Arg Pro Gln Leu Leu Pro Leu Leu Leu
```

```
              1               5                  10                 15
            Leu Leu Cys Gly Gly Cys Pro Arg Ala Gly Gly Cys Asn Glu Thr Gly
                            20                 25                 30

Met Leu Glu Arg Leu Pro Leu Cys Gly Lys Ala Phe Ala Asp Met Met
                            35                 40                 45

Gly Lys Val Asp Val Trp Lys Trp Cys Asn Leu Ser Glu Phe Ile Val
                    50                 55                 60

Tyr Tyr Glu Ser Phe Thr Asn Cys Thr Glu Met Glu Ala Asn Val Val
            65                 70                 75                 80

Gly Cys Tyr Trp Pro Asn Pro Leu Ala Gln Gly Phe Ile Thr Gly Ile
                                85                 90                 95

His Arg Gln Phe Phe Ser Asn Cys Thr Val Asp Arg Val His Leu Glu
                            100                105                110

Asp Pro Pro Asp Glu Val Leu Ile Pro Leu Ile Val Ile Pro Val Val
                            115                120                125

Leu Thr Val Ala Met Ala Gly Leu Val Val Trp Arg Ser Lys Arg Thr
                    130                135                140

Asp Thr Leu Leu
            145

<210> SEQ ID NO 7
<211> LENGTH: 279
<212> TYPE: DNA
<213> ORGANISM: Homo sapiens

<400> SEQUENCE: 7
ctgcctgcca ggaggctaac tacggtgccc tcctccggga gctctgcctc acccagttcc      60
aggtagacat ggaggccgtc ggggagacgc tgtggtgtga ctggggcagg accatcagga     120
gctacaggga gctggccgac tgcacctggc acatggcgga gaagctgggc tgcttctggc     180
ccaatgcaga ggtggcaggt tcttcctggc agtgcatggc cgctacttca ggagctgccc     240
catctcaggc agggccgtgc gggacccgcc cggcagcat                            279

<210> SEQ ID NO 8
<211> LENGTH: 93
<212> TYPE: PRT
<213> ORGANISM: Homo sapiens

<400> SEQUENCE: 8

Ala Cys Gln Glu Ala Asn Tyr Gly Ala Leu Leu Arg Glu Leu Cys Leu
            1               5                  10                 15

Thr Gln Phe Gln Val Asp Met Glu Ala Val Gly Glu Thr Leu Trp Cys
                            20                 25                 30

Asp Trp Gly Arg Thr Ile Arg Ser Tyr Arg Glu Leu Ala Asp Cys Thr
                            35                 40                 45

Trp His Met Ala Glu Lys Leu Gly Cys Phe Trp Pro Asn Ala Glu Val
                    50                 55                 60

Asp Arg Phe Phe Leu Ala Val His Gly Arg Tyr Phe Arg Ser Cys Pro
            65                 70                 75                 80

Ile Ser Gly Arg Ala Val Arg Asp Pro Pro Gly Ser Ile
                            85                 90

<210> SEQ ID NO 9
<211> LENGTH: 330
<212> TYPE: DNA
<213> ORGANISM: Homo sapiens
```

-continued

<400> SEQUENCE: 9

```
aatccccacg aggccctggc tcagcctctt cccaccacag gcacaccagg gtcagaaggg    60
gggacggtga agaactatga gacagctgtc caattttgct ggaatcatta taaggatcaa   120
atggatccta tcgaaaagga ttggtgcgac tgggccatga ttagcaggcc ttatagcacc   180
ctgcgagatt gcctggagca ctttgcagag ttgtttgacc tgggcttccc caatcccttg   240
gcagagagga tcatctttga gactcaccag atccactttg ccaactgctc cctggtgcag   300
cccaccttct ctgaccccccc agaggatgta                                    330
```

<210> SEQ ID NO 10
<211> LENGTH: 116
<212> TYPE: PRT
<213> ORGANISM: Homo sapiens

<400> SEQUENCE: 10

```
Leu Gly Ala Val Leu Asn Pro His Glu Ala Leu Ala Gln Pro Leu Pro
1               5                   10                  15

Thr Thr Gly Thr Pro Gly Ser Glu Gly Gly Thr Val Lys Asn Tyr Glu
            20                  25                  30

Thr Ala Val Gln Phe Cys Trp Asn His Tyr Lys Asp Gln Met Asp Pro
        35                  40                  45

Ile Glu Lys Asp Trp Cys Asp Trp Ala Met Ile Ser Arg Pro Tyr Ser
    50                  55                  60

Thr Leu Arg Asp Cys Leu Glu His Phe Ala Glu Leu Phe Asp Leu Gly
65                  70                  75                  80

Phe Pro Asn Pro Leu Ala Glu Arg Ile Ile Phe Glu Thr His Gln Ile
                85                  90                  95

His Phe Ala Asn Cys Ser Leu Val Gln Pro Thr Phe Ser Asp Pro Pro
            100                 105                 110

Glu Asp Val Leu
        115
```

<210> SEQ ID NO 11
<211> LENGTH: 346
<212> TYPE: DNA
<213> ORGANISM: Homo sapiens

<400> SEQUENCE: 11

```
cagagcaggc ggctgcaacg agacaggcat gttggagagg ctgcccctgt gtgggaaggc    60
tttcgcagac atgatgggca aggtggacgt ctggaagtgg tgcaacctgt ccgagttcat   120
cgtgtactat gagagtttca ccaactgcac cgagatggag gccaatgtcg tgggctgcta   180
ctggcccaac cccctggccc agggcttcat caccggcatc acaggcagt tcttctccaa    240
ctgcaccgtg gacagggtcc acttggagga cccccagac gaggttctca tcccgctgat    300
cgttataccc gtcgttctga ctgtcgccat ggctggcctg gtggtg                  346
```

<210> SEQ ID NO 12
<211> LENGTH: 98
<212> TYPE: PRT
<213> ORGANISM: Homo sapiens

<400> SEQUENCE: 12

```
Gly Cys Pro Arg Ala Gly Gly Cys Asn Glu Thr Gly Met Leu Glu Arg
1               5                   10                  15

Leu Pro Leu Cys Gly Lys Ala Phe Ala Asp Met Met Gly Lys Val Asp
            20                  25                  30
```

```
Val Trp Lys Trp Cys Asn Leu Ser Glu Phe Ile Val Tyr Tyr Glu Ser
        35                  40                  45

Phe Thr Asn Cys Thr Glu Met Glu Ala Asn Val Val Gly Cys Tyr Trp
    50                  55                  60

Pro Asn Pro Leu Ala Gln Gly Phe Ile Thr Gly Ile His Arg Gln Phe
65                  70                  75                  80

Phe Ser Asn Cys Thr Val Asp Arg Val His Leu Glu Asp Pro Pro Asp
                85                  90                  95

Glu Val

<210> SEQ ID NO 13
<211> LENGTH: 150
<212> TYPE: DNA
<213> ORGANISM: homo sapiens

<400> SEQUENCE: 13
ctgcctgcca ggaggctaac tacggtgccc tcctccggga gctctgcctc acccagttcc      60
aggtagacat ggaggccgtc ggggagacgc tgtggtgtga ctggggcagg accatcagga     120
gctacaggga gctggccgac tgcacctggc                                      150

<210> SEQ ID NO 14
<211> LENGTH: 50
<212> TYPE: PRT
<213> ORGANISM: Homo sapiens

<400> SEQUENCE: 14

Ala Cys Gln Glu Ala Asn Tyr Gly Ala Leu Leu Arg Glu Leu Cys Leu
1               5                   10                  15

Thr Gln Phe Gln Val Asp Met Glu Ala Val Gly Glu Thr Leu Trp Cys
            20                  25                  30

Asp Trp Gly Arg Thr Ile Arg Ser Tyr Arg Glu Leu Ala Asp Cys Thr
        35                  40                  45

Trp His
    50

<210> SEQ ID NO 15
<211> LENGTH: 90
<212> TYPE: DNA
<213> ORGANISM: Homo sapiens

<400> SEQUENCE: 15
ctgcctgcca ggaggctaac tacggtgccc tcctccggga gctctgcctc acccagttcc      60
aggtagacat ggaggccgtc ggggagacgc                                       90

<210> SEQ ID NO 16
<211> LENGTH: 30
<212> TYPE: PRT
<213> ORGANISM: Homo sapiens

<400> SEQUENCE: 16

Ala Cys Gln Glu Ala Asn Tyr Gly Ala Leu Leu Arg Glu Leu Cys Leu
1               5                   10                  15

Thr Gln Phe Gln Val Asp Met Glu Ala Val Gly Glu Thr Leu
            20                  25                  30

<210> SEQ ID NO 17
<211> LENGTH: 60
<212> TYPE: DNA
```

<213> ORGANISM: Homo sapiens

<400> SEQUENCE: 17
ctgcctgcca ggaggctaac tacggtgccc tcctccggga gctctgcctc acccagttcc    60

<210> SEQ ID NO 18
<211> LENGTH: 20
<212> TYPE: PRT
<213> ORGANISM: Homo sapiens

<400> SEQUENCE: 18

Ala Cys Gln Glu Ala Asn Tyr Gly Ala Leu Leu Arg Glu Leu Cys Leu
1               5                   10                  15

Thr Gln Phe Gln
            20

<210> SEQ ID NO 19
<211> LENGTH: 123
<212> TYPE: DNA
<213> ORGANISM: Homo sapiens

<400> SEQUENCE: 19
ccctcctccg ggagctctgc ctcacccagt tccaggtaga catggaggcc gtcggggaga    60
cgctgtggtg tgactggggc aggaccatca ggagctacag ggagctggcc gactgcacct   120
ggc                                                                 123

<210> SEQ ID NO 20
<211> LENGTH: 40
<212> TYPE: PRT
<213> ORGANISM: Homo sapiens

<400> SEQUENCE: 20

Leu Arg Glu Leu Cys Leu Thr Gln Phe Gln Val Asp Met Glu Ala Val
1               5                   10                  15

Gly Glu Thr Leu Trp Cys Asp Trp Gly Arg Thr Ile Arg Ser Tyr Arg
            20                  25                  30

Glu Leu Ala Asp Cys Thr Trp His
        35                  40

<210> SEQ ID NO 21
<211> LENGTH: 93
<212> TYPE: DNA
<213> ORGANISM: Homo sapiens

<400> SEQUENCE: 21
tccaggtaga catggaggcc gtcggggaga cgctgtggtg tgactggggc aggaccatca    60
ggagctacag ggagctggcc gactgcacct ggc                                 93

<210> SEQ ID NO 22
<211> LENGTH: 29
<212> TYPE: PRT
<213> ORGANISM: Homo sapiens

<400> SEQUENCE: 22

Met Glu Ala Val Gly Glu Thr Leu Trp Cys Asp Trp Gly Arg Thr Ile
1               5                   10                  15

Arg Ser Tyr Arg Glu Leu Ala Asp Cys Thr Trp His Met
            20                  25

<210> SEQ ID NO 23

<211> LENGTH: 189
<212> TYPE: DNA
<213> ORGANISM: Homo sapiens

<400> SEQUENCE: 23

| cgctgtggtg | tgactggggc | aggaccatca | ggagctacag | ggagctggcc | gactgcacct | 60 |
| ggcacatggc | ggagaagctg | gctgcttct | ggcccaatgc | agaggtggca | ggttcttcct | 120 |
| ggcagtgcat | ggccgctact | tcaggagctg | ccccatctca | ggcagggccg | tgcgggaccc | 180 |
| gcccggcag | | | | | | 189 |

<210> SEQ ID NO 24
<211> LENGTH: 65
<212> TYPE: PRT
<213> ORGANISM: Homo sapiens

<400> SEQUENCE: 24

Val Gly Glu Thr Leu Trp Cys Asp Trp Gly Arg Thr Ile Arg Ser Tyr
1               5                   10                  15

Arg Glu Leu Ala Asp Cys Thr Trp His Met Ala Glu Lys Leu Gly Cys
            20                  25                  30

Phe Trp Pro Asn Ala Glu Val Asp Arg Phe Phe Leu Ala Val His Gly
        35                  40                  45

Arg Tyr Phe Arg Ser Cys Pro Ile Ser Gly Arg Ala Val Arg Asp Pro
    50                  55                  60

Pro
65

<210> SEQ ID NO 25
<211> LENGTH: 124
<212> TYPE: DNA
<213> ORGANISM: Homo sapiens

<400> SEQUENCE: 25

| ggagctacag | ggagctggcc | gactgcacct | ggcacatggc | ggagaagctg | gctgcttct | 60 |
| ggcccaatgc | agaggtggca | ggttcttcct | ggcagtgcat | ggccgctact | tcaggagctg | 120 |
| cccc | | | | | | 124 |

<210> SEQ ID NO 26
<211> LENGTH: 45
<212> TYPE: PRT
<213> ORGANISM: Homo sapiens

<400> SEQUENCE: 26

Arg Thr Ile Arg Ser Tyr Arg Glu Leu Ala Asp Cys Thr Trp His Met
1               5                   10                  15

Ala Glu Lys Leu Gly Cys Phe Trp Pro Asn Ala Glu Val Asp Arg Phe
            20                  25                  30

Phe Leu Ala Val His Gly Arg Tyr Phe Arg Ser Cys Pro
        35                  40                  45

<210> SEQ ID NO 27
<211> LENGTH: 132
<212> TYPE: DNA
<213> ORGANISM: Homo sapiens

<400> SEQUENCE: 27

| ggcacatggc | ggagaagctg | gctgcttct | ggcccaatgc | agaggtggca | ggttcttcct | 60 |
| ggcagtgcat | ggccgctact | tcaggagctg | ccccatctca | ggcagggccg | tgcgggaccc | 120 |

```
gcccggcagc at                                                           132

<210> SEQ ID NO 28
<211> LENGTH: 42
<212> TYPE: PRT
<213> ORGANISM: Homo sapiens

<400> SEQUENCE: 28

Ala Glu Lys Leu Gly Cys Phe Trp Pro Asn Ala Glu Val Asp Arg Phe
1               5                   10                  15

Phe Leu Ala Val His Gly Arg Tyr Phe Arg Ser Cys Pro Ile Ser Gly
            20                  25                  30

Arg Ala Val Arg Asp Pro Pro Gly Ser Ile
        35                  40

<210> SEQ ID NO 29
<211> LENGTH: 150
<212> TYPE: DNA
<213> ORGANISM: Homo sapiens

<400> SEQUENCE: 29
aatccccacg aggccctggc tcagcctctt cccaccacag gcacaccagg gtcagaaggg      60
gggacggtga agaactatga gacagctgtc caattttgct ggaatcatta taaggatcaa    120
atggatccta tcgaaaagga ttggtgcgac                                     150

<210> SEQ ID NO 30
<211> LENGTH: 50
<212> TYPE: PRT
<213> ORGANISM: Homo sapiens

<400> SEQUENCE: 30

Leu Gly Ala Val Leu Asn Pro His Glu Ala Leu Ala Gln Pro Leu Pro
1               5                   10                  15

Thr Thr Gly Thr Pro Gly Ser Glu Gly Gly Thr Val Lys Asn Tyr Glu
            20                  25                  30

Thr Ala Val Gln Phe Cys Trp Asn His Tyr Lys Asp Gln Met Asp Pro
        35                  40                  45

Ile Glu
    50

<210> SEQ ID NO 31
<211> LENGTH: 90
<212> TYPE: DNA
<213> ORGANISM: Homo sapiens

<400> SEQUENCE: 31
aatccccacg aggccctggc tcagcctctt cccaccacag gcacaccagg gtcagaaggg      60
gggacggtga agaactatga gacagctgtc                                      90

<210> SEQ ID NO 32
<211> LENGTH: 30
<212> TYPE: PRT
<213> ORGANISM: Homo sapiens

<400> SEQUENCE: 32

Leu Gly Ala Val Leu Asn Pro His Glu Ala Leu Ala Gln Pro Leu Pro
1               5                   10                  15

Thr Thr Gly Thr Pro Gly Ser Glu Gly Gly Thr Val Lys Asn
            20                  25                  30
```

<210> SEQ ID NO 33
<211> LENGTH: 60
<212> TYPE: DNA
<213> ORGANISM: Homo sapiens

<400> SEQUENCE: 33
aatccccacg aggccctggc tcagcctctt cccaccacag gcacaccagg gtcagaaggg    60

<210> SEQ ID NO 34
<211> LENGTH: 20
<212> TYPE: PRT
<213> ORGANISM: Homo sapiens

<400> SEQUENCE: 34

Leu Gly Ala Val Leu Asn Pro His Glu Ala Leu Ala Gln Pro Leu Pro
1               5                   10                  15

Thr Thr Gly Thr
            20

<210> SEQ ID NO 35
<211> LENGTH: 123
<212> TYPE: DNA
<213> ORGANISM: Homo sapiens

<400> SEQUENCE: 35
cttcccacca caggcacacc agggtcagaa gggggggacgg tgaagaacta tgagacagct    60
gtccaatttt gctggaatca ttataaggat caaatggatc ctatcgaaaa ggattggtgc   120
gac                                                                123

<210> SEQ ID NO 36
<211> LENGTH: 40
<212> TYPE: PRT
<213> ORGANISM: Homo sapiens

<400> SEQUENCE: 36

Leu Ala Gln Pro Leu Pro Thr Thr Gly Thr Pro Gly Ser Glu Gly Gly
1               5                   10                  15

Thr Val Lys Asn Tyr Glu Thr Ala Val Gln Phe Cys Trp Asn His Tyr
            20                  25                  30

Lys Asp Gln Met Asp Pro Ile Glu
        35                  40

<210> SEQ ID NO 37
<211> LENGTH: 30
<212> TYPE: PRT
<213> ORGANISM: Homo sapiens

<400> SEQUENCE: 37

Pro Gly Ser Glu Gly Gly Thr Val Lys Asn Tyr Glu Thr Ala Val Gln
1               5                   10                  15

Phe Cys Trp Asn His Tyr Lys Asp Gln Met Asp Pro Ile Glu
            20                  25                  30

<210> SEQ ID NO 38
<211> LENGTH: 214
<212> TYPE: DNA
<213> ORGANISM: Homo sapiens

<400> SEQUENCE: 38
gtccaatttt gctggaatca ttataaggat caaatggatc ctatcgaaaa ggattggtgc    60

```
gactgggcca tgattagcag gccttatagc accctgcgag attgcctgga gcactttgca      120
gagttgtttg acctgggctt ccccaatccc ttggcagaga ggatcatctt tgagactcac      180
cagatccact tgccaactg ctccctggtg cagc                                    214
```

<210> SEQ ID NO 39
<211> LENGTH: 70
<212> TYPE: PRT
<213> ORGANISM: Homo sapiens

<400> SEQUENCE: 39

```
Tyr Glu Thr Ala Val Gln Phe Cys Trp Asn His Tyr Lys Asp Gln Met
1               5                   10                  15

Asp Pro Ile Glu Lys Asp Trp Cys Asp Trp Ala Met Ile Ser Arg Pro
                20                  25                  30

Tyr Ser Thr Leu Arg Asp Cys Leu Glu His Phe Ala Glu Leu Phe Asp
            35                  40                  45

Leu Gly Phe Pro Asn Pro Leu Ala Glu Arg Ile Ile Phe Glu Thr His
        50                  55                  60

Gln Ile His Phe Ala Asn
65                  70
```

<210> SEQ ID NO 40
<211> LENGTH: 184
<212> TYPE: DNA
<213> ORGANISM: Homo sapiens

<400> SEQUENCE: 40

```
caaatggatc ctatcgaaaa ggattggtgc gactgggcca tgattagcag gccttatagc      60
accctgcgag attgcctgga gcactttgca gagttgtttg acctgggctt ccccaatccc     120
ttggcagaga ggatcatctt tgagactcac cagatccact tgccaactg ctccctggtg     180 cagc                                                                   184
```

<210> SEQ ID NO 41
<211> LENGTH: 60
<212> TYPE: PRT
<213> ORGANISM: Homo sapiens

<400> SEQUENCE: 41

```
His Tyr Lys Asp Gln Met Asp Pro Ile Glu Lys Asp Trp Cys Asp Trp
1               5                   10                  15

Ala Met Ile Ser Arg Pro Tyr Ser Thr Leu Arg Asp Cys Leu Glu His
                20                  25                  30

Phe Ala Glu Leu Phe Asp Leu Gly Phe Pro Asn Pro Leu Ala Glu Arg
            35                  40                  45

Ile Ile Phe Glu Thr His Gln Ile His Phe Ala Asn
        50                  55                  60
```

<210> SEQ ID NO 42
<211> LENGTH: 154
<212> TYPE: DNA
<213> ORGANISM: Homo sapiens

<400> SEQUENCE: 42

```
gactgggcca tgattagcag gccttatagc accctgcgag attgcctgga gcactttgca      60
gagttgtttg acctgggctt ccccaatccc ttggcagaga ggatcatctt tgagactcac     120
cagatccact tgccaactg ctccctggtg cagc                                   154
```

<210> SEQ ID NO 43
<211> LENGTH: 60
<212> TYPE: PRT
<213> ORGANISM: Homo sapiens

<400> SEQUENCE: 43

Lys Asp Trp Cys Asp Trp Ala Met Ile Ser Arg Pro Tyr Ser Thr Leu
1               5                   10                  15

Arg Asp Cys Leu Glu His Phe Ala Glu Leu Phe Asp Leu Gly Phe Pro
            20                  25                  30

Asn Pro Leu Ala Glu Arg Ile Ile Phe Glu Thr His Gln Ile His Phe
        35                  40                  45

Ala Asn Cys Ser Leu Val Gln Pro Thr Phe Ser Asp
    50                  55                  60

<210> SEQ ID NO 44
<211> LENGTH: 124
<212> TYPE: DNA
<213> ORGANISM: Homo sapiens

<400> SEQUENCE: 44
accctgcgag attgcctgga gcactttgca gagttgtttg acctgggctt ccccaatccc      60
ttggcagaga ggatcatctt tgagactcac cagatccact tgccaactg ctccctggtg     120 cagc                                                                 124

<210> SEQ ID NO 45
<211> LENGTH: 50
<212> TYPE: PRT
<213> ORGANISM: Homo sapiens

<400> SEQUENCE: 45

Arg Pro Tyr Ser Thr Leu Arg Asp Cys Leu Glu His Phe Ala Glu Leu
1               5                   10                  15

Phe Asp Leu Gly Phe Pro Asn Pro Leu Ala Glu Arg Ile Ile Phe Glu
            20                  25                  30

Thr His Gln Ile His Phe Ala Asn Cys Ser Leu Val Gln Pro Thr Phe
        35                  40                  45

Ser Asp
    50

<210> SEQ ID NO 46
<211> LENGTH: 94
<212> TYPE: DNA
<213> ORGANISM: Homo sapiens

<400> SEQUENCE: 46
gagttgtttg acctgggctt ccccaatccc ttggcagaga ggatcatctt tgagactcac      60
cagatccact tgccaactg ctccctggtg cagc                                  94

<210> SEQ ID NO 47
<211> LENGTH: 30
<212> TYPE: PRT
<213> ORGANISM: Homo sapiens

<400> SEQUENCE: 47

Glu His Phe Ala Glu Leu Phe Asp Leu Gly Phe Pro Asn Pro Leu Ala
1               5                   10                  15

Glu Arg Ile Ile Phe Glu Thr His Gln Ile His Phe Ala Asn

-continued

```
                    20                  25                  30
```

<210> SEQ ID NO 48
<211> LENGTH: 150
<212> TYPE: DNA
<213> ORGANISM: Homo sapiens

<400> SEQUENCE: 48

```
cagagcaggc ggctgcaacg agacaggcat gttggagagg ctgcccctgt gtgggaaggc    60
tttcgcagac atgatgggca aggtggacgt ctggaagtgg tgcaacctgt ccgagttcat   120
cgtgtactat gagagtttca ccaactgcac                                    150
```

<210> SEQ ID NO 49
<211> LENGTH: 50
<212> TYPE: PRT
<213> ORGANISM: Homo sapiens

<400> SEQUENCE: 49

```
Gly Cys Pro Arg Ala Gly Gly Cys Asn Glu Thr Gly Met Leu Glu Arg
 1               5                  10                  15

Leu Pro Leu Cys Gly Lys Ala Phe Ala Asp Met Met Gly Lys Val Asp
                20                  25                  30

Val Trp Lys Trp Cys Asn Leu Ser Glu Phe Ile Val Tyr Tyr Glu Ser
         35                  40                  45

Phe Thr
     50
```

<210> SEQ ID NO 50
<211> LENGTH: 120
<212> TYPE: DNA
<213> ORGANISM: Homo sapiens

<400> SEQUENCE: 50

```
cagagcaggc ggctgcaacg agacaggcat gttggagagg ctgcccctgt gtgggaaggc    60
tttcgcagac atgatgggca aggtggacgt ctggaagtgg tgcaacctgt ccgagttcat   120
```

<210> SEQ ID NO 51
<211> LENGTH: 40
<212> TYPE: PRT
<213> ORGANISM: Homo sapiens

<400> SEQUENCE: 51

```
Gly Cys Pro Arg Ala Gly Gly Cys Asn Glu Thr Gly Met Leu Glu Arg
 1               5                  10                  15

Leu Pro Leu Cys Gly Lys Ala Phe Ala Asp Met Met Gly Lys Val Asp
                20                  25                  30

Val Trp Lys Trp Cys Asn Leu Ser
         35                  40
```

<210> SEQ ID NO 52
<211> LENGTH: 90
<212> TYPE: DNA
<213> ORGANISM: Homo sapiens

<400> SEQUENCE: 52

```
cagagcaggc ggctgcaacg agacaggcat gttggagagg ctgcccctgt gtgggaaggc    60
tttcgcagac atgatgggca aggtggacgt                                     90
```

<210> SEQ ID NO 53

```
<211> LENGTH: 30
<212> TYPE: PRT
<213> ORGANISM: Homo sapiens

<400> SEQUENCE: 53

Gly Cys Pro Arg Ala Gly Gly Cys Asn Glu Thr Gly Met Leu Glu Arg
1               5                   10                  15
Leu Pro Leu Cys Gly Lys Ala Phe Ala Asp Met Met Gly Lys
            20                  25                  30

<210> SEQ ID NO 54
<211> LENGTH: 63
<212> TYPE: DNA
<213> ORGANISM: Homo sapiens

<400> SEQUENCE: 54
catcgtgtac tatgagagtt tcaccaactg caccgagatg gaggccaatg tcgtgggctg    60
cta                                                                  63

<210> SEQ ID NO 55
<211> LENGTH: 20
<212> TYPE: PRT
<213> ORGANISM: Homo sapiens

<400> SEQUENCE: 55

Glu Phe Ile Val Tyr Tyr Glu Ser Phe Thr Asn Cys Thr Glu Met Glu
1               5                   10                  15
Ala Asn Val Val
            20

<210> SEQ ID NO 56
<211> LENGTH: 63
<212> TYPE: DNA
<213> ORGANISM: Homo sapiens

<400> SEQUENCE: 56
caccgagatg gaggccaatg tcgtgggctg ctactggccc aaccccctgg cccagggctt    60
cat                                                                  63

<210> SEQ ID NO 57
<211> LENGTH: 20
<212> TYPE: PRT
<213> ORGANISM: Homo sapiens

<400> SEQUENCE: 57

Asn Cys Thr Glu Met Glu Ala Asn Val Val Gly Cys Tyr Trp Pro Asn
1               5                   10                  15
Pro Leu Ala Gln
            20

<210> SEQ ID NO 58
<211> LENGTH: 84
<212> TYPE: DNA
<213> ORGANISM: Homo sapiens

<400> SEQUENCE: 58
caccgagatg gaggccaatg tcgtgggctg ctactggccc aaccccctgg cccagggctt    60
catcaccggc atccacaggc agtt                                           84

<210> SEQ ID NO 59
<211> LENGTH: 30
```

```
<212> TYPE: PRT
<213> ORGANISM: Homo sapiens

<400> SEQUENCE: 59

Asn Cys Thr Glu Met Glu Ala Asn Val Val Gly Cys Tyr Trp Pro Asn
1               5                   10                  15

Pro Leu Ala Gln Gly Phe Ile Thr Gly Ile His Arg Gln Phe
            20                  25                  30

<210> SEQ ID NO 60
<211> LENGTH: 114
<212> TYPE: DNA
<213> ORGANISM: Homo sapiens

<400> SEQUENCE: 60
caccgagatg gaggccaatg tcgtgggctg ctactggccc aaccccctgg cccagggctt      60
catcaccggc atccacaggc agttcttctc caactgcacc gtggacaggg tcca          114

<210> SEQ ID NO 61
<211> LENGTH: 40
<212> TYPE: PRT
<213> ORGANISM: Homo sapiens

<400> SEQUENCE: 61

Asn Cys Thr Glu Met Glu Ala Asn Val Val Gly Cys Tyr Trp Pro Asn
1               5                   10                  15

Pro Leu Ala Gln Gly Phe Ile Thr Gly Ile His Arg Gln Phe Phe Ser
            20                  25                  30

Asn Cys Thr Val Asp Arg Val His
            35                  40

<210> SEQ ID NO 62
<211> LENGTH: 199
<212> TYPE: DNA
<213> ORGANISM: Homo sapiens

<400> SEQUENCE: 62
caccgagatg gaggccaatg tcgtgggctg ctactggccc aaccccctgg cccagggctt      60
catcaccggc atccacaggc agttcttctc caactgcacc gtggacaggg tccacttgga    120 ggaccccca gacgaggttc tcatcccgct gatcgttata cccgtcgttc tgactgtcgc     180
catggctggc ctggtggtg                                                 199

<210> SEQ ID NO 63
<211> LENGTH: 48
<212> TYPE: PRT
<213> ORGANISM: Homo sapiens

<400> SEQUENCE: 63

Asn Cys Thr Glu Met Glu Ala Asn Val Val Gly Cys Tyr Trp Pro Asn
1               5                   10                  15

Pro Leu Ala Gln Gly Phe Ile Thr Gly Ile His Arg Gln Phe Phe Ser
            20                  25                  30

Asn Cys Thr Val Asp Arg Val His Leu Glu Asp Pro Pro Asp Glu Val
            35                  40                  45

<210> SEQ ID NO 64
<211> LENGTH: 2984
<212> TYPE: DNA
<213> ORGANISM: Homo sapiens
```

```
<400> SEQUENCE: 64
gaacaacctc tctctctcca gcagagagtg tcacctcctg ctttaggacc atcaagctct      60
gctaactgaa tctcatccta attgcaggat cacattgcaa agctttcact ctttcccacc     120
ttgcttgtgg gtaaatctct tctgcggaat ctcagaaagt aaagttccat cctgagaata     180
tttcacaaag aatttcctta agagctggac tgggtcttga cccctgaatt taagaaattc     240
ttaaagacaa tgtcaaatat gatccaagag aaaatgtgat ttgagtctgg agacaattgt     300
gcatatcgtc taataataaa aacccatact agcctataga aaacaatatt tgaaagattg     360
ctaccactaa aaagaaaact actacaactt gacaagactg ctgcaaactt caatttgtca     420
accacaactt gacaaggttg ctataaaaca agattgctac aacttctagt ttatgttata     480
cagcatattt cattttggct taatgatgga gaaaaagtgt accctgtatt ttctggttct     540
cttgcctttt tttatgattc ttgttacagc agaattagaa gagagtcctg aggactcaat     600
tcagttggga gttactagaa ataaaatcat gacagctcaa tatgaatgtt accaaaagat     660
tatgcaagac cccattcaac aagcagaagg cgtttactgc aacagaacct gggatggatg     720
gctctgctgg aacgatgttg cagcaggaac tgaatcaatg cagctctgcc ctgattactt     780
tcaggacttt gatccatcag aaaaagttac aaagatctgt gaccaagatg aaactggtt      840
tagacatcca gcaagcaaca gaacatggac aaattatacc cagtgtaatg ttaacaccca     900
cgagaaagtg aagactgcac taaatttgtt ttacctgacc ataattggac acggattgtc     960
tattgcatca ctgcttatct cgcttggcat attctttat ttcaagagcc taagttgcca    1020
aaggattacc ttacacaaaa atctgttctt ctcatttgtt tgtaactctg ttgtaacaat    1080
cattcacctc actgcagtgg ccaacaacca ggccttagta gccacaaatc ctgttagttg    1140
caaagtgtcc cagttcattc atctttacct gatgggctgt aattactttt ggatgctctg    1200
tgaaggcatt tacctacaca cactcattgt ggtggccgtg tttgcagaga agcaacattt    1260
aatgtggtat tattttcttg gctggggatt tccactgatt cctgcttgta tacatgccat    1320
tgctagaagc ttatattaca atgacaattg ctggatcagt tctgataccc atctcctcta    1380
cattatccat ggcccaattt gtgctgcttt actggtgaat ctttttttct tgttaaatat    1440
tgtacgcgtt ctcatcacca agttaaaagt tacacaccaa gcggaatcca atctgtacat    1500
gaaagctgtg agagctactc ttatcttggt gccattgctt ggcattgaat ttgtgctgat    1560
tccatggcga cctgaaggaa agattgcaga ggaggtatat gactacatca tgcacatcct    1620
tatgcacttc cagggtcttt tggtctctac cattttctgc ttctttaatg gagaggttca    1680
agcaattctg agaagaaact ggaatcaata caaaatccaa tttggaaaca gcttttccaa    1740
ctcagaagct cttcgtagtg cgtcttacac agtgtcaaca atcagtgatg gtccaggtta    1800
tagtcatgac tgtcctagtg aacacttaaa tggaaaaagc atccatgata ttgaaaatgt    1860
tctcttaaaa ccagaaaatt tatataattg aaaatagaag gatggttgtc tcactgtttt    1920
gtgcttctcc taactcaagg acttggaccc atgactctgt agccagaaga cttcaatatt    1980
aaatgacttt ttgaatgtca taagaagag ccttcacatg aaattagtag tgtgttgata    2040
agagtgtaac atccagctct atgtgggaaa aagaaatcc tggtttgtaa tgtttgtcag    2100
taaatactcc cactatgcct gatgtgacgc tactaacctg acatcaccaa gtgtggaatt    2160
ggagaaaagc acaatcaact tttctgagct ggtgtaagcc agttccagca caccattgca    2220
tgaattcaca aacaaatggc tgtaaaacta acatacatg ttgggcatga ttctacccctt    2280
attgccccaa gagacctagc taaggtctat aaacatgaag ggaaaattag ctttttagttt    2340
```

```
taaaactctt tatcccatct tgattggggc agttgacttt ttttttgccc agagtgccgt    2400
agtccttttt gtaactaccc tctcaaatgg acaataccag aagtgaatta tccctgctgg    2460
ctttcttttc tctatgaaaa gcaactgagt acaattgtta tgatctactc atttgctgac    2520
acatcagtta tatcttgtgg catatccatt gtggaaactg gatgaacagg atgtataata    2580
tgcaatccta cttctatatc attaggaaaa catcttagtt gatgctacaa acaccttgt     2640 caacctcttc ctgtcttacc aaacagtggg agggaattcc tagctgtaaa tataaatttt    2700
gtcccttcca tttctactgt ataaacaaat tagcaatcat tttatataaa gaaaatcaat    2760
gaaggatttc ttattttctt ggaattttgt aaaaagaaat tgtgaaaaat gagcttgtaa    2820
atactccatt attttatttt atagtctcaa atcaaataca tacaacctat gtaatttta    2880 aagcaaatat ataatgcaac aatgtgtgta tgttaatatc tgatactgta tctgggctga    2940
ttttttaaat aaaatagagt ctggaatgct aaaaaaaaaa aaaa                    2984
```

<210> SEQ ID NO 65
<211> LENGTH: 461
<212> TYPE: PRT
<213> ORGANISM: Homo sapiens

<400> SEQUENCE: 65

```
Met Glu Lys Lys Cys Thr Leu Tyr Phe Leu Val Leu Leu Pro Phe Phe
1               5                   10                  15

Met Ile Leu Val Thr Ala Glu Leu Glu Glu Ser Pro Glu Asp Ser Ile
                20                  25                  30

Gln Leu Gly Val Thr Arg Asn Lys Ile Met Thr Ala Gln Tyr Glu Cys
            35                  40                  45

Tyr Gln Lys Ile Met Gln Asp Pro Ile Gln Gln Ala Glu Gly Val Tyr
        50                  55                  60

Cys Asn Arg Thr Trp Asp Gly Trp Leu Cys Trp Asn Asp Val Ala Ala
65                  70                  75                  80

Gly Thr Glu Ser Met Gln Leu Cys Pro Asp Tyr Phe Gln Asp Phe Asp
                85                  90                  95

Pro Ser Glu Lys Val Thr Lys Ile Cys Asp Gln Asp Gly Asn Trp Phe
            100                 105                 110

Arg His Pro Ala Ser Asn Arg Thr Trp Thr Asn Tyr Thr Gln Cys Asn
        115                 120                 125

Val Asn Thr His Glu Lys Val Lys Thr Ala Leu Asn Leu Phe Tyr Leu
    130                 135                 140

Thr Ile Ile Gly His Gly Leu Ser Ile Ala Ser Leu Leu Ile Ser Leu
145                 150                 155                 160

Gly Ile Phe Phe Tyr Phe Lys Ser Leu Ser Cys Gln Arg Ile Thr Leu
                165                 170                 175

His Lys Asn Leu Phe Phe Ser Phe Val Cys Asn Ser Val Val Thr Ile
            180                 185                 190

Ile His Leu Thr Ala Val Ala Asn Asn Gln Ala Leu Val Ala Thr Asn
        195                 200                 205

Pro Val Ser Cys Lys Val Ser Gln Phe Ile His Leu Tyr Leu Met Gly
    210                 215                 220

Cys Asn Tyr Phe Trp Met Leu Cys Glu Gly Ile Tyr Leu His Thr Leu
225                 230                 235                 240

Ile Val Val Ala Val Phe Ala Glu Lys Gln His Leu Met Trp Tyr Tyr
                245                 250                 255
```

```
Phe Leu Gly Trp Gly Phe Pro Leu Ile Pro Ala Cys Ile His Ala Ile
                260                 265                 270

Ala Arg Ser Leu Tyr Tyr Asn Asp Asn Cys Trp Ile Ser Ser Asp Thr
            275                 280                 285

His Leu Leu Tyr Ile Ile His Gly Pro Ile Cys Ala Ala Leu Leu Val
        290                 295                 300

Asn Leu Phe Phe Leu Leu Asn Ile Val Arg Val Leu Ile Thr Lys Leu
305                 310                 315                 320

Lys Val Thr His Gln Ala Glu Ser Asn Leu Tyr Met Lys Ala Val Arg
                325                 330                 335

Ala Thr Leu Ile Leu Val Pro Leu Leu Gly Ile Glu Phe Val Leu Ile
            340                 345                 350

Pro Trp Arg Pro Glu Gly Lys Ile Ala Glu Glu Val Tyr Asp Tyr Ile
        355                 360                 365

Met His Ile Leu Met His Phe Gln Gly Leu Leu Val Ser Thr Ile Phe
    370                 375                 380

Cys Phe Phe Asn Gly Glu Val Gln Ala Ile Leu Arg Arg Asn Trp Asn
385                 390                 395                 400

Gln Tyr Lys Ile Gln Phe Gly Asn Ser Phe Ser Asn Ser Glu Ala Leu
                405                 410                 415

Arg Ser Ala Ser Tyr Thr Val Ser Thr Ile Ser Asp Gly Pro Gly Tyr
            420                 425                 430

Ser His Asp Cys Pro Ser Glu His Leu Asn Gly Lys Ser Ile His Asp
        435                 440                 445

Ile Glu Asn Val Leu Leu Lys Pro Glu Asn Leu Tyr Asn
450                 455                 460

<210> SEQ ID NO 66
<211> LENGTH: 39
<212> TYPE: PRT
<213> ORGANISM: Homo sapiens

<400> SEQUENCE: 66

Gly Cys Pro Arg Ala Gly Gly Cys Asn Glu Thr Gly Met Leu Glu Arg
1               5                   10                  15

Leu Pro Leu Cys Gly Lys Ala Phe Ala Asp Met Met Gly Lys Val Asp
                20                  25                  30

Val Trp Lys Trp Cys Asn Leu
        35

<210> SEQ ID NO 67
<211> LENGTH: 53
<212> TYPE: PRT
<213> ORGANISM: Homo sapiens

<400> SEQUENCE: 67

Glu Ser Phe Thr Asn Cys Thr Glu Met Glu Ala Asn Val Val Gly Cys
1               5                   10                  15

Tyr Trp Pro Asn Pro Leu Ala Gln Gly Phe Ile Thr Gly Ile His Arg
                20                  25                  30

Gln Phe Phe Ser Asn Cys Thr Val Asp Arg Val His Leu Glu Asp Pro
            35                  40                  45

Pro Asp Glu Val Leu
        50

<210> SEQ ID NO 68
<211> LENGTH: 21
```

```
<212> TYPE: DNA
<213> ORGANISM: Artificial
<220> FEATURE:
<223> OTHER INFORMATION: siRNA

<400> SEQUENCE: 68
tggcccatca cctcttcatg a                                              21

<210> SEQ ID NO 69
<211> LENGTH: 21
<212> TYPE: DNA
<213> ORGANISM: Artificial
<220> FEATURE:
<223> OTHER INFORMATION: siRNA

<400> SEQUENCE: 69
ctggctgctc ctggcccatc a                                              21

<210> SEQ ID NO 70
<211> LENGTH: 21
<212> TYPE: DNA
<213> ORGANISM: Artificial
<220> FEATURE:
<223> OTHER INFORMATION: siRNA

<400> SEQUENCE: 70
tcctggccca tcacctcttc a                                              21

<210> SEQ ID NO 71
<211> LENGTH: 19
<212> TYPE: DNA
<213> ORGANISM: Artificial
<220> FEATURE:
<223> OTHER INFORMATION: siRNA

<400> SEQUENCE: 71
cuaugagaca gcuguccaa                                                 19

<210> SEQ ID NO 72
<211> LENGTH: 19
<212> TYPE: DNA
<213> ORGANISM: Artificial
<220> FEATURE:
<223> OTHER INFORMATION: siRNA

<400> SEQUENCE: 72
guucuucucc aacugcacc                                                 19

<210> SEQ ID NO 73
<211> LENGTH: 21
<212> TYPE: DNA
<213> ORGANISM: Artificial
<220> FEATURE:
<223> OTHER INFORMATION: Oligonucleotide Primer Sequence

<400> SEQUENCE: 73
cgagcggact cgactcggca c                                              21

<210> SEQ ID NO 74
<211> LENGTH: 21
<212> TYPE: DNA
<213> ORGANISM: Artificial
<220> FEATURE:
<223> OTHER INFORMATION: Oligonucleotide Primer Sequence

<400> SEQUENCE: 74
```
cttcctaggg tggcggtggc c         21

<210> SEQ ID NO 75
<211> LENGTH: 20
<212> TYPE: DNA
<213> ORGANISM: Artificial
<220> FEATURE:
<223> OTHER INFORMATION: Oligonucleotide Primer Sequence

<400> SEQUENCE: 75
gtccgcctcc tccttctgct         20

<210> SEQ ID NO 76
<211> LENGTH: 23
<212> TYPE: DNA
<213> ORGANISM: Artificial
<220> FEATURE:
<223> OTHER INFORMATION: Oligonucleotide Primer Sequence

<400> SEQUENCE: 76
aagtggagta acatggttat tgt         23

<210> SEQ ID NO 77
<211> LENGTH: 23
<212> TYPE: DNA
<213> ORGANISM: Artificial
<220> FEATURE:
<223> OTHER INFORMATION: Oligonucleotide Primer Sequence

<400> SEQUENCE: 77
agccatggag actggagcgc tgc         23

<210> SEQ ID NO 78
<211> LENGTH: 24
<212> TYPE: DNA
<213> ORGANISM: Artificial
<220> FEATURE:
<223> OTHER INFORMATION: Oligonucleotide Primer Sequence

<400> SEQUENCE: 78
gtggcccagt agctggagat tggc         24

<210> SEQ ID NO 79
<211> LENGTH: 23
<212> TYPE: DNA
<213> ORGANISM: Artificial
<220> FEATURE:
<223> OTHER INFORMATION: Oligonucleotide Primer Sequence

<400> SEQUENCE: 79
gcgaattcct gccagaccac cag         23

<210> SEQ ID NO 80
<211> LENGTH: 24
<212> TYPE: DNA
<213> ORGANISM: Artificial
<220> FEATURE:
<223> OTHER INFORMATION: Oligonucleotide Primer Sequence

<400> SEQUENCE: 80
gtggatccta ccgggcccgg gaca         24

<210> SEQ ID NO 81
<211> LENGTH: 34
<212> TYPE: DNA
<213> ORGANISM: Artificial

```
<220> FEATURE:
<223> OTHER INFORMATION: Oligonucleotide Primer Sequence

<400> SEQUENCE: 81
gcgaattcaa tccccacgag gccctggctc agcc                                34

<210> SEQ ID NO 82
<211> LENGTH: 33
<212> TYPE: DNA
<213> ORGANISM: Artificial
<220> FEATURE:
<223> OTHER INFORMATION: Oligonucleotide Primer Sequence

<400> SEQUENCE: 82
caggatccta caagagtgat gaggaagggg atg                                 33

<210> SEQ ID NO 83
<211> LENGTH: 35
<212> TYPE: DNA
<213> ORGANISM: Artificial
<220> FEATURE:
<223> OTHER INFORMATION: Oligonucleotide Primer Sequence

<400> SEQUENCE: 83
cagaatttcc agagcaggcc gctgcaacca gacag                               35

<210> SEQ ID NO 84
<211> LENGTH: 35
<212> TYPE: DNA
<213> ORGANISM: Artificial
<220> FEATURE:
<223> OTHER INFORMATION: Oligonucleotide Primer Sequence

<400> SEQUENCE: 84
gtggatccca ccaccaggcc agccatggcg acagt                               35
```

THERAPEUTIC AGENT

REFERENCE TO RELATED APPLICATIONS

This application is divisional of U.S. patent application Ser. No. 12/849,536 filed Aug. 3, 2010, which is a continuation of U.S. patent application Ser. No. 12/090,635 filed Apr. 17, 2008, which is the US national phase entry of International Patent Application No. PCT/GB2006/050338 filed Oct. 18, 2006, which claims priority to GB Patent Application No. 0521139.6 filed Oct. 18, 2005.

TECHNICAL FIELD

The invention relates to therapeutic agents based on cell surface polypeptides involved in adrenomedullin mediated signaling and to screening assays to identify therapeutic agents.

BACKGROUND

Cell signaling is crucial for survival; without it physically or chemically isolated cells undergo apoptosis. In cancer cells many contact dependent processes are aberrant, but it has been shown that reception of adrenomedullin-mediated signaling is an essential for survival of cells in 80% of tumors. While many hormones and cytokines bind to specific receptors, adrenomedullin (AM) acts through a receptor known as the Calcitonin Receptor Like Receptor (CRLR).

The calcitonin family of bioactive peptides comprises of calcitonin, amylin, two Calcitonin-Gene Related Peptides (CGRP1, and CGRP2) and adrenomedullin (AM). Calcitonin is 32 amino acid peptide found in the parafollicular "C" cells of the thyroid in mammals as well as in a number of non-mammals. Calcitonin regulates the mineral (calcium and phosphate) balance. Calcitonin causes hypercalcemia by acting as an inhibitor of osteoclast induced bone resorption. CGRP is a 37 amino acid peptide produced by tissue specific processing of the calcitonin gene. Calcitonin is the major product in the thyroid, whereas CGRP is the major product in neural tissues. CGRP is a potent cardiovascular agent and has structural similarity with amylin. CGRP is found in two isoforms (CGRP-I and CGRP-II) that differ only by 3 amino acids.

Adrenomedullin (AM) is a 52 amino acid hypotensive peptide. It has structural similarity with CGRP and amylin. AM is produced in peripheral tissues, adrenal medulla, lung, and kidney and it is unregulated in ischaemia. Receptors for AM exist in many tissues, for example in astrocytes in the central nervous system, in the iris muscle in the eye, in bone, blood vessels, the heart, kidney and skin (Uchikawa et al., Clin. Exp. Pharmacol. Physiol. 2005 August; 32(8):675-80; Sumanas et al., Blood. 2005 Jul. 15; 106(2):534-41; Cornish J, Reid J Musculoskelet. Neuronal Interact. 2001 September; 2(1):15-24; Yoshihara et al., Regul. Pept. 2005 Apr. 15; 127(1-3):239-44; Matsumoto et al., Clin. Exp. Nephrol. 2004 December; 8(4):316-21; Muller et al., Br J. Dermatol. 2003 January; 148(1):30-8). In general, the calcitonin family of peptides has N-terminal ring structures of 6-7 amino acids involving a disulfide and an amidated C-terminal end.

The calcitonin family of peptides act through G-protein coupled membrane receptors (GPCRs). The gene for calcitonin receptors has been cloned. It is homologous to GPCRs in family "B" which typically recognize regulatory peptides (secretin, glucagons, VIP). A homolog of the calcitonin receptor, the Calcitonin Receptor Like Receptor (CRLR, also known as CL) has been identified (human 461 aa; rat/mouse 463 aa) and has 55% homology with calcitonin receptor (Njuki et al., Clin. Sci. 85, 385-388 (1993); Chang et al., Neuron 11, 1187-1195 (1993); Fluhmann et al., Biochem. Biophys. Res. Commun. 206, 341-347 (1995); Kapas et al., J. Biol. Chem. 270, 25344-25347 (1995)). Two related members of the family "A" class of GPCR, RDC1 and G10D, were identified as receptors for CGRP and AM, respectively.

Alone, the CRLR is unable to transduce a signal in response to AM, as the presence of a RAMP (Receptor Activity Modifying Protein) is needed to induce ligand specificity, binding and activation of the CRLR. The RAMPs are family of small intrinsic membrane proteins, with a predicted sizes of 14,000-17,0000 Kd. RAMPs consists of approximately 120 amino acids with a large extracellular domains of around 100 amino acids; a single membrane spanning domain and a short intra-cellular region of approximately 10 amino acids.

It has been shown that CRLR can function as either a CGRP receptor or an AM receptor, depending upon which members of the RAMP family, RAMPs1-3, are expressed. RAMP1, 2 and 3 contain an N-terminal signal peptide, an extracellular N-terminus, a single transmembrane domain near the C-terminus, and cytoplasmic C-terminus. RAMP1-3 displays 31% identity. RAMP-2 and RAMP-3 have approximately 30% identity. RAMPS may be involved in the transport of CRLR to the plasma membrane.

The three members of the RAMP family, RAMP1, 2 and 3, engender different ligand specificities of the CRLR so that:

RAMP1+CRLR=CGRP receptor
RAMP2+CRLR=AM receptor
RAMP3+CRLR=AM receptor

RAMP1 presents CRLR at the plasma membrane as a terminally glycosylated, mature glycoprotein and a CGRP receptor, whereas RAMPs 2 and 3 present CRLR as an immature, core glycosylated ADM receptor (McLatchie et al., 1998).

The present invention relates to the identification of therapeutic agents with the ability to influence RAMP-CLRL interactions. Such agents are targets for, inter alia, cancer therapy.

SUMMARY

In a first aspect of the present invention, there is provided an agent that is capable of binding to and/or modulating an effect of a calcitonin receptor-like receptor (CRLR) of one or more RAMP proteins (Receptor Activity Modifying Protein) selected from (i) a RAMP-3, (ii) a RAMP-2 and (iii) RAMP-1 protein.

In an embodiment, the agent binds to an extracellular domain of a RAMP protein. In a particular embodiment, the RAMP protein is a human RAMP protein. Particularly, the agent may be capable of modulating interaction of RAMP-3 and CRLR.

In one embodiment, the agent of the present invention binds at least one ligand selected from:
 (a) a peptide moiety of 1 to 31 amino acid residues including a sequence of contiguous amino acid residues comprised in the sequence of contiguous amino acids from position 1 to position 31 of a human RAMP-3 protein as shown in FIG. 3 (SEQ ID NO: 6);
 (b) a peptide moiety of 1 to 15 amino acid residues including a sequence of contiguous amino acid residues comprised in the sequence of contiguous amino acids from position 32 to position 46 of a human RAMP-3 protein as shown in FIG. 3 (SEQ ID NO: 6); and (c) a peptide moiety of 1 to 53 amino acid residues including a sequence of contiguous amino acid residues comprised in the sequence of contiguous amino acids from position 47 to position 99 of human RAMP-3 protein as shown in FIG. 3 (SEQ ID NO: 6).

In one embodiment, the agent binds to at least one ligand selected from:

(a) a peptide moiety of 1 to 32 amino acid residues including a sequence of contiguous amino acid residues comprised in the sequence of contiguous amino acids from position 1 to position 32 of a human RAMP-3 protein as shown in FIG. 3 (SEQ ID NO: 6);

(b) a peptide moiety of 1 to 14 amino acid residues including a sequence of contiguous amino acid residues comprised in the sequence of contiguous amino acids from position 33 to position 46 of a human RAMP-3 protein as shown in FIG. 3 (SEQ ID NO: 6); and (c) a peptide moiety of 1 to 53 amino acid residues including a sequence of contiguous amino acid residues comprised in the sequence of contiguous amino acids from position 47 to position 99 of human RAMP-3 protein as shown in FIG. 3 (SEQ ID NO: 6).

Typically, the peptide moiety is between 5 and 15 amino acids long. Peptide moieties (a), (b) and (c) independently of one another may have 5, 6, 7, 8, 9, 10, 11, 12, 13 or 14 amino acid residues. They can have 5 to 13, 5 to 11 or 5 to 9 residues e.g. 13 amino acid residues, 11 amino acid residues or 9 residues. Also, within the scope of the invention are peptide moieties (a), (b) and (c) having (independently of one another) 5, 6, 7, 8, 10, 12, 14 or 15 amino acid residues. Larger numbers of amino acid residues for peptide moieties of (a), (b) and (c) are possible including 17, 18, 19, 20, 25 or 30 residues. Peptide moiety (c) may have larger numbers of amino acid residues including, for example, 31, 32, 35, 40, 45, 50 and 53 amino acid residues. The agent of the present invention may bind to an epitope which comprises at least one peptide moiety described herein.

Peptide moiety (b) may include all or part of a putative CRLR binding domain. The agent may bind to a fragment of a human RAMP-3 which is produced by enzyme digestion of a RAMP-3 extracellular domain using human caspase-3 and human calpain-1.

Also included in the present disclosure are agents which bind to at least one peptide moiety selected from:

(a) a peptide moiety of 1 to 15 amino acid residues including a sequence of contiguous amino acid residues comprised in the following amino acid sequence: GCPRAGGCNE TGMLERLPLC GKAFADMMGK VDVWKWCNL (SEQ ID NO: 66); and (b) a peptide moiety of 1 to 15 amino acid residues including a sequence of contiguous amino acid residues comprised in the following amino acid sequence: ESFT NCTEMEANVV GCYWPNPLAQ GFITGIHRQF FSNCTVDRVH LEDPPDEVL (SEQ ID NO: 67).

The sequences shown above are contained within a RAMP-3 protein, which comprises, for example, the amino acid sequence of FIG. 3 (SEQ ID NO: 6).

The agent of the present disclosure optionally has one or more of the following two capabilities:

1. it is capable of inhibiting proliferation of a SW-13 cell which expresses said RAMP and CRLR proteins by at least 10%, wherein said proliferation is measured using a MTT Cell Proliferation Assay; and/or 2. it is capable of inhibiting cAMP production in a human MG63 osteosarcoma cell, in response to administration of adrenomedullin, by at least about 15% as compared to administration of adrenomedullin in the absence of the agent.

The agent may be capable of binding to a RAMP protein, e.g. RAMP-3. In one embodiment, the agent binds to the extracellular domain of RAMP-3, e.g. a sequence comprising amino acid residues 1 to 99 of FIG. 3 (SEQ ID NO: 6).

The data disclosed herein may indicate that inhibitors of either the interaction between RAMP-3 and CRLR on the one hand or the interaction between a RAMP-3/CRLR associated complex and a ligand such as adrenomedullin may have use in the prevention of cancer and angiogenesis. Such an agent may also have use in the treatment of diabetes, including alleviating the symptoms of diabetes e.g. diabetic microangiopathies.

According to an aspect of the invention there is provided an agent that modulates the effect of a polypeptide on calcitonin receptor like receptor (CRLR) function wherein said polypeptide is selected from the group consisting of:

i) a polypeptide, or variant thereof, encoded by a nucleic acid molecule consisting of a nucleic acid sequence as represented by FIG. 1, 2 or 3 (SEQ ID NO: 1, 3 or 5, respectively);

ii) a polypeptide encoded by a nucleic acid molecule which hybridizes under stringent conditions to a nucleic acid molecule as defined in (i) above and which modulates CRLR function; and iii) a polypeptide comprising a nucleic acid which is degenerate as a result of the genetic code to the nucleic acid sequence defined in (i) and (ii), characterized in that said agent is for use as a pharmaceutical.

As used herein "CRLR function or activity" refers to any biological activity of CRLR. A specific "function" includes CRLR activation in response to a ligand, examples of which include adrenomedullin (AM) and CGRP. Typically, CRLR activation in response to AM or CGRP induces cAMP expression and the activation of other second messenger systems.

Since a ligand such as AM or CGRP will bind to the polypeptide of the invention i.e. a RAMP protein, only when the polypeptide is associated with CRLR, the agents according to the invention can be used to modulate, for example interfere with, the association of the RAMP protein with CRLR. By interfering with the association of the RAMP protein e.g. RAMP-1, RAMP-2 and RAMP-3 with CRLR, CRLR activation can be affected, for example, reduced or even prevented. Said interference may be for example as a result of direct or indirect blocking of a ligand binding site on the RAMP protein, on the CRLR and/or within a complex of RAMP/CRLR. In one embodiment, the agent binds to an amino acid sequence of an extracellular domain of RAMP-3 protein which is not the CRLR binding region. In an alternative embodiment, the agent may be an agonist, that is to say, mimics the interaction of the RAMP/CRLR receptor with a ligand, and therefore may lead to stimulation of the CRLR receptor and increased or unusual signaling by the receptor.

In a preferred embodiment, the agent is an antibody product. In one embodiment, the antibody product binds to a RAMP-3 protein. The antibody may specifically bind to RAMP-3.

Encompassed within the scope of the present disclosure is the agent for use as a pharmaceutical.

In further aspects of the present invention, there are provided vectors which are adapted for the expression of an agent of the present invention when the agent is, for example, an antibody product or a protein e.g. a fusion protein. The present invention also provides a cell which has been transformed or transfected with a vector as described herein.

In a further aspect of the present invention, there is provided a method of producing an agent as described herein for example an antibody.

DETAILED DESCRIPTION

The following terms and abbreviations are used in this specification:

Definitions

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Definitions and additional information known to one of skill in the art in immunology can be found, for example, in Fundamental Immunology, W. E. Paul, ed., fourth edition, Lippincott-Raven Publishers, 1999.

Antibody fragment (fragment with specific antigen binding): Various fragments of antibodies have been defined, including Fab, (Fab')$_2$, Fv, dsFV, single-chain Fv (scFv) and domain antibodies, including single domain antibodies. These antibody fragments are defined as follows: (1) Fab, the fragment that contains a monovalent antigen-binding fragment of an antibody molecule produced by digestion of whole antibody with the enzyme papain to yield an intact light chain and a portion of one heavy chain or equivalently by genetic engineering; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction or equivalently by genetic engineering; (4) F(Ab')$_2$, a dimer of two FAb' fragments held together by disulfide bonds; (5) Fv, a genetically engineered fragment containing the variable region of the light chain and the variable region of the heavy chain expressed as two chains; dsFV, which is the variable region of the light chain and the variable region of the heavy chain linked by disulfide bonds and (6) single chain antibody ("SCA"), a genetically engineered molecule containing the variable region of the light chain, the variable region of the heavy chain, linked by a suitable polypeptide linker as a genetically fused single chain molecule. Single chain antibodies may also be referred to as single chain variable fragments (scFv).

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit and bovine. A single domain antibody may be a naturally occurring single domain antibody known as heavy chain antibody devoid of light chains. Such single domain antibodies are disclosed in WO 9404678 for example. Methods of making these fragments are routine in the art.

dAB (domain antibodies) are the smallest functional binding units of antibodies, corresponding to the variable regions of either the heavy (VH) or light (VL) chains of human antibodies. Domain Antibodies have a molecular weight of approximately 13 kDa, or less than one-tenth the size of a full antibody. Domain antibodies may include dAbs which bind to two therapeutic targets. These include: IgG-like molecules; PEGylated fusion proteins; and anti-serum albumin fusion proteins. In the IgG-like antibody, two variable domains bind to two therapeutic targets on each arm of the IgG.

Cell line/Cell culture: A "cell line" or "cell culture" denotes higher eukaryotic cells grown or maintained in vitro. It is understood that the progeny of a cell may not be completely identical (either morphologically, genotypically, or phenotypically) to the parent cell. "Heterologous" means derived from a genotypically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence with which it is not naturally found linked is a heterologous promoter. An "isolated" polynucleotide or polypeptide is one that is substantially free of the materials with which it is associated in nature. By substantially free is meant at least 50%, preferably at least 70%, more preferably at least 80%, and even more preferably at least 90% free of the materials with which it is associated in nature.

Complementarity-determining region (CDR): The CDRs are three hypervariable regions within each of the variable light (VL) and variable heavy (VH) regions of an antibody molecule that form the antigen-binding surface that is complementary to the three-dimensional structure of the bound antigen. Proceeding from the N-terminus of a heavy or light chain, these complementarity-determining regions are denoted as "CDR1", "CDR2," and "CDR3," respectively. CDRs are involved in antigen-antibody binding, and the CDR3 comprises a unique region specific for antigen-antibody binding. An antigen-binding site, therefore, may include six CDRs, comprising the CDR regions from each of a heavy and a light chain V region. Alteration of a single amino acid within a CDR region can alter the affinity of an antibody for a specific antigen (see Abbas et al., *Cellular and Molecular Immunology*, 4th ed. 143-5, 2000). The locations of the CDRs have been precisely defined, e.g., by Kabat et al., *Sequences of Proteins of Immunologic Interest*, U.S. Department of Health and Human Services, 1983. The light and heavy chains of an Ig each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest*, 5$^{th}$ Edition, Department of Health and Human Services, Public Health Service, National Institutes of Health, Bethesda (NIH Publication No. 91-3242).

Reference is made to the numbering scheme from Kabat, E. A., et al., Sequences of Proteins of Immunological Interest (National Institutes of Health, Bethesda, Md. (1987)

and (1991). In these compendiums, Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. For purposes of this invention, to assign residue numbers to a candidate antibody amino acid sequence which is not included in the Kabat compendium, one follows the following steps. Generally, the candidate sequence is aligned with any immunoglobulin sequence or any consensus sequence in Kabat. Alignment may be done by hand, or by computer using commonly accepted computer programs; an example of such a program is the Align 2 program discussed in this description. Alignment may be facilitated by using some amino acid residues which are common to most Fab sequences. For example, the light and heavy chains each typically have two cysteines which have the same residue numbers; in VL domain the two cysteines are typically at residue numbers 23 and 88, and in the VH domain the two cysteine residues are typically numbered 22 and 92. Framework residues generally, but not always, have approximately the same number of residues, however the CDRs will vary in size. For example, in the case of a CDR from a candidate sequence which is longer than the CDR in the sequence in Kabat to which it is aligned, typically suffixes are added to the residue number to indicate the insertion of additional residues (see, e.g. residues 100abcde in FIG. 5). For candidate sequences which, for example, align with a Kabat sequence for residues 34 and 36 but have no residue between them to align with residue 35, the number 35 is simply not assigned to a residue.

CDR and FR residues are also determined according to a structural definition (as in Chothia and Lesk, J. Mol. Biol. 196:901-917 (1987). Where these two methods result in slightly different identifications of a CDR, the structural definition is preferred, but the residues identified by the sequence definition method are considered important FR residues for determination of which framework residues to import into a consensus sequence.

Constant Region: The portion of the antibody molecule which confers effector functions. In the present disclosure, the variant antibodies of use can include constant regions derived from human immunoglobulins. The heavy chain constant region can be selected from any of five isotypes: alpha, delta, epsilon, gamma or mu. Heavy chains of various subclasses (such as the IgG subclass of heavy chains) are responsible for different effector functions. Thus, by choosing the desired heavy chain constant region, humanized antibodies with the desired effector function can be produced. The light chain constant region can be of the kappa or lambda type.

Epitope: The site on an antigen recognized by an agent as determined by the specificity of the amino acid sequence. Two agents are said to bind to the same epitope if each competitively inhibits (blocks) binding of the other to the antigen as measured in a competitive binding assay (see, e.g., Junghans et al., *Cancer Res.* 50:1495-1502, 1990). Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

Framework region (FR): Relatively conserved sequences flanking the three highly divergent complementarity-determining regions (CDRs) within the variable regions of the heavy and light chains of an antibody. Hence, the variable region of an antibody heavy or light chain consists of a FR and three CDRs. Some FR residues may contact bound antigen; however, FRs are primarily responsible for folding the variable region into the antigen-binding site, particularly the FR residues directly adjacent to the CDRs. Without being bound by theory, the framework regions serve to hold the CDRs in an appropriate orientation for antigen binding. The numbering of the residues in the light chain and heavy chain framework regions follows the numbering convention delineated by Kabat et al., (1991, supra). The sequences of the framework regions of different light or heavy chains are relatively conserved within a species. A "human" framework region is a framework region that is substantially identical (about 85% or more, usually 90-95% or more) to the framework region of a naturally occurring human immunoglobulin.

Inhibit: A species which retards, blocks or prevents an interaction, for example (i) binding between a RAMP protein and a ligand or (ii) association between a RAMP protein and a CRLR or (iiI) binding of a RAMP/CRLR complex with a ligand, is considered to inhibit the interaction. Typically, inhibition does not result in 100% blockage but rather reduces the amount and/or speed of interaction.

Immunogenicity: A measure of the ability of a targeting protein, a therapeutic moiety or an agent to elicit an immune response (humoral or cellular) when administered to a subject.

Immunoglobulin: Immunoglobulin (Ig) molecules and immunologically active portions of Ig molecules, for instance, molecules that contain an antigen binding site which specifically binds (immunoreacts with) an antigen. The term "antibody" may also be used.

A naturally occurring antibody or immunoglobulin (for example, IgG) includes four polypeptide chains, two heavy (H) chains and two light (L) chains interconnected by disulfide bonds. The two heavy chains are linked to each other by disulfide bonds and each heavy chain is linked to a light chain by a disulfide bond. There are two types of light chain, lambda (λ) and kappa (k). There are five main heavy chain classes (or isotypes) which determine the functional activity of an antibody molecule: IgM, IgD, IgG, IgA and IgE. Full-length immunoglobulin light chains are generally about 25 Kd or 214 amino acids in length. Full-length immunoglobulin heavy chains are generally about 50 Kd or 446 amino acid in length. Light chains are encoded by a variable region gene at the NH2-terminus (about 110 amino acids in length) and a kappa or lambda constant region gene at the COOH-terminus. Heavy chains are similarly encoded by a variable region gene (about 116 amino acids in length) and one of the other constant region genes.

The basic structural unit of an antibody is generally a tetramer that consists of two identical pairs of immunoglobulin chains, each pair having one light and one heavy chain. In each pair, the light and heavy chain variable regions bind to an antigen, and the constant regions mediate effector functions. Immunoglobulins also exist in a variety of other forms including, for example, Fv, Fab, and (Fab')$_2$, as well as bifunctional hybrid antibodies and single chains (e.g., Lanzavecchia et al., *Eur. J. Immunol.* 17:105, 1987; Huston et al., *Proc. Natl. Acad. Sci. U.S.A.,* 85:5879-5883, 1988; Bird et al., *Science* 242:423-426, 1988; Hood et al., *Immunology*, Benjamin, N.Y., 2nd ed., 1984; Hunkapiller and Hood, *Nature* 323:15-16, 1986).

Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors. An immunoglobulin light or heavy chain variable region includes a framework region interrupted by three hypervariable regions, also called complementarity determining regions (CDR's) (see, *Sequences of Proteins of Immunological Interest*, E. Kabat et al., U.S. Department of Health and Human Services, 1983). As noted above, the CDRs are primarily responsible for binding to an epitope of an antigen. The specificity of the antibody resides in the structural complementarity between the antibody combining site and the antigenic determinant.

Chimeric antibodies are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments, such as kappa and gamma 1 or gamma 3. In one example, a therapeutic chimeric antibody is thus a hybrid protein composed of the variable or antigen-binding domain from a mouse antibody and the constant or effector domain from a human antibody, although other mammalian species can be used, or the variable region can be produced by molecular techniques. Methods of making chimeric antibodies are well known in the art, e.g., see U.S. Pat. No. 5,807,715, which is herein incorporated by reference.

A "humanized" immunoglobulin or antibody is an immunoglobulin including a human framework region and one or more CDRs from a non-human (such as a mouse, rat, or synthetic) immunoglobulin. The non-human immunoglobulin providing the CDRs is termed a "donor" and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Exemplary conservative substitutions are those such as gly, ala; val, ile, leu; asp, glu; asn, gln; ser, thr; lys, arg; and phe, tyr (see U.S. Pat. No. 5,585,089, which is incorporated herein by reference). Humanized immunoglobulins can be constructed by means of genetic engineering, e.g., see U.S. Pat. No. 5,225,539 and U.S. Pat. No. 5,585,089, which are herein incorporated by reference.

A human antibody is an antibody wherein the light and heavy chain genes are of human origin. Human antibodies can be generated using methods known in the art. Human antibodies can be produced by immortalizing a human B cell secreting the antibody of interest. Immortalization can be accomplished, for example, by EBV infection or by fusing a human B cell with a myeloma or hybridoma cell to produce a trioma cell. Human antibodies can also be produced by phage display methods (see, e.g., Dower et al., PCT Publication No. WO91/17271; McCafferty et al., PCT Publication No. WO92/001047; and Winter, PCT Publication No. WO92/20791, which are herein incorporated by reference), or selected from a human combinatorial monoclonal antibody library (see the Morphosys website). Human antibodies can also be prepared by using transgenic animals carrying a human immunoglobulin gene (e.g., see Lonberg et al., PCT Publication No. WO93/12227; and Kucherlapati, PCT Publication No. WO91/10741, which are herein incorporated by reference).

Antibodies may also be obtained using phage display technology. Phase display technology is known in the art for example Marks et al., J. Mol. Biol. 222: 581-597 and Ckackson et al., Nature 352: 624-628, both incorporated herein by reference. Phage display technology can also be used to increase the affinity of an antibody. To increase antibody affinity, the antibody sequence is diversified, a phage antibody library is constructed, and a higher affinity binders are selected on antigen (see for example Marks et al., Bio/Technology 10:779-783, Barbas et al Proc. Natl. Acad. Sci USA 91:3809-3813 and Schier et al., J. Mol. Biol. 263: 551-567, all incorporated herein by reference).

Aptamer: The agent of the present invention may also be an aptamer. Aptamers have been defined as artificial nucleic acid ligands that can be generated against amino acids, drugs, proteins and other molecules. They are isolated from complex libraries of synthetic nucleic acids by an iterative process of adsorption, recovery and re-amplification.

RNA aptamers are nucleic acid molecules with affinities for specific target molecules. They have been likened to antibodies because of their ligand binding properties. They may be considered as useful agents for a variety of reasons. Specifically, they are soluble in a wide variety of solution conditions and concentrations, and their binding specificities are largely undisturbed by reagents such as detergents and other mild denaturants. Moreover, they are relatively cheap to isolate and produce. They may also readily be modified to generate species with improved properties. Extensive studies show that nucleic acids are largely non-toxic and non-immunogenic and aptamers have already found clinical application. Furthermore, it is known how to modulate the activities of aptamers in biological samples by the production of inactive dsRNA molecules in the presence of complementary RNA single strands (Rusconi et al., 2002).

It is known from the prior art how to isolate aptamers from degenerate sequence pools by repeated cycles of binding, sieving and amplification. Such methods are described in U.S. Pat. No. 5,475,096, U.S. Pat. No. 5,270, 163 and EP0533 38, and typically are referred to as SELEX (Systematic Evolution of Ligands by EX-ponential Enrichment). The basic SELEX system has been modified for example by using Photo-SELEX where aptamers contain photo-reactive groups capable of binding and/or photo cross-linking to and/or photo-activating or inactivating a target molecule. Other modifications include Chimeric-SELEX, Blended-SELEX, Counter-SELEX, Solution-SELEX, Chemi-SELEX, Tissue-SELEX and Transcription-free SELEX which describes a method for ligating random fragments of RNA bound to a DNA template to form the oligonucleotide library. However, these methods even though producing enriched ligand-binding nucleic acid molecules, still produce unstable products. In order to overcome the problem of stability it is known to create enantiomeric "spiegelmers" (WO 01/92566). The process involves initially creating a chemical mirror image of the target, then selecting aptamers to this mirror image and finally creating a chemical mirror image of the SELEX selected aptamer. By selecting natural RNAs, based on D-ribose sugar units, against the non-natural enantiomer of the eventual target molecule, for example a peptide made of D-amino acids, a spiegelmer directed against the natural L-amino acid target can be created. Once tight binding aptamers to the non-natural enantiomer target are isolated and sequenced, the Laws of Molecular Symmetry mean that RNAs synthesized chemically based on L-ribose sugars will bind the natural target, that is to say the mirror image of the selection target. This process is conveniently referred to as reflection-selection or mirror selection and the L-ribose species produced are significantly more stable in biological environments because they are less susceptible to normal enzymatic cleavage, i.e. they are nuclease resistant.

Immunoreactivity: A measure of the ability of an agent, sometimes an antibody, to recognize and bind to a specific antigen. "Specifically binds" refers to the ability of individual agents or antibodies to specifically immunoreact with an antigen. This binding is a non-random binding reaction between an agent, for example but not limited to an antibody molecule, and the antigen. Binding specificity is typically determined from the reference point of the ability of the agent to differentially bind the antigen of interest and an unrelated antigen, and therefore distinguish between two different antigens, particularly where the two antigens have unique epitopes.

Typically, specificity may be determined by means of a binding assay such as ELISA employing a panel of antigens. An agent according to the present invention may recognize a RAMP protein, e.g. RAMP-1, RAMP-2 or RAMP-3 on cells.

Monoclonal antibody: is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Generally, a monoclonal antibody is produced by a specific hybridoma cell, or a progeny of the hybridoma cell propagated in culture. A hybridoma or other cell producing an antibody may be subject to genetic mutation or other changes, which may or may not alter the binding specificity of antibodies produced.

Nucleic Acid: A "nucleic acid" is a polymeric form of nucleotides of any length, which contain deoxyribonucleotides, ribonucleotides, and analogs in any combination. Nucleic acids may have any three-dimensional structure, and may perform any function, known or unknown. The term "nucleic acid" includes double-, single-stranded, and triple-helical molecules. Unless otherwise specified or required, any embodiment of the invention described herein that is a nucleic acid encompasses both the double-stranded form and each of two complementary single-stranded forms known or predicted to make up the double stranded form.

Polypeptide: The terms "polypeptide", "peptide" and "protein" are used interchangeably herein to refer to polymers of amino acids of any length. The polymer may be linear or branched, it may comprise modified amino acids or amino acid analogs, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component.

Amino acid substitutions can range from changing or modifying one or more amino acids to complete redesign of a region, such as the variable region. Amino acid substitutions are preferably conservative substitutions that do not deleteriously affect folding or functional properties of the peptide. Groups of functionally related amino acids within which conservative substitutions may be made are glycine/alanine; valine/isoleucine/leucine; asparagine/glutamine; aspartic acid/glutamic acid; serine/threonine/methionine; lysine/arginine; and phenylalanine/tyrosine/tryptophan. Polypeptides of this invention may be in glycosylated or unglycosylated form, may be modified post-translationally (e.g., acetylation, and phosphorylation) or may be modified synthetically (e.g., the attachment of a labeling group).

As used herein, a "variant" polypeptide may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and asparatic acid; c) asparagine and glutamine d) arginine and lysine; e) isoleucine, leucine, methionine and valine and f) phenylalanine, tyrosine and tryptophan.

As mentioned above, a first aspect of the present invention provides an agent which is capable of binding to and or modulating an effect an a calcitonin receptor-like receptor (CRLR) of one or more RAMP proteins (Receptor Activity Modifying Protein) selected from (i) a RAMP-3, (ii) a RAMP-2 and (iii) RAMP-1 protein.

In an embodiment, the agent binds to an extracellular domain of a RAMP protein. Typically, the agent is capable of modulating interaction of RAMP-3 and CRLP.

In an embodiment, the agent is capable of inhibiting proliferation of a human SW-13 cell by at least 10%, wherein said inhibition is measured using a MTT Cell Proliferation assay. Preferably, the agent is capable of modulating e.g. interfering with, interaction of RAMP-3 and CRLP.

Typically, the agent is capable of inhibiting proliferation by at least 12%. In some embodiments, the agent may be capable of inhibiting proliferation by at least 20% and optionally at least 25%. In a further embodiment, the agent may be capable of inhibiting proliferation by at least 30% and further optionally at least 40%.

In one embodiment, the agent is capable of reducing or inhibiting production of cAMP in a human MG63 osteosarcoma cell, when stimulated by adrenomedullin, by at least about 15%, e.g. at least 15%, 16%, 17%, 18% and 19%. In some embodiments, the agent may be capable of inhibiting production of cAMP by at least about 20% e.g. 21%, 22% or 25%. Typically, the agent is capable of modulating an interaction of RAMP-3 and CRLP.

The agent of the present disclosure may modulate an effect of a RAMP protein, the RAMP protein being selected from;

i) a polypeptide, or variant thereof, encoded by a nucleic acid molecule consisting of a nucleic acid sequence as represented by FIG. 1 (SEQ ID NO: 1);
ii) a polypeptide encoded by a nucleic acid molecule which hybridizes under stringent conditions to a nucleic acid molecule as defined in (i) above and which modulates CRLR function; and
iii) a polypeptide comprising a nucleic acid which is degenerate as a result of the genetic code to the nucleic acid sequence defined in (i) and (ii), characterized in that said agent is for use as a pharmaceutical, and wherein the RAMP-2 protein is selected from:
i) a polypeptide, or variant thereof, encoded by a nucleic acid molecule consisting of a nucleic acid sequence as represented by FIG. 2 (SEQ ID NO: 3);
ii) a polypeptide encoded by a nucleic acid molecule which hybridizes under stringent conditions to a nucleic acid molecule as defined in (i) above and which modulates CRLR function; and
iii) a polypeptide comprising a nucleic acid which is degenerate as a result of the genetic code to the nucleic acid sequence defined in (i) and (ii), characterized in that said agent is for use as a pharmaceutical, and further wherein the RAMP-3 protein is selected from:
i) a polypeptide, or variant thereof, encoded by a nucleic acid molecule consisting of a nucleic acid sequence as represented by FIG. 3 (SEQ ID NO: 5);
ii) a polypeptide encoded by a nucleic acid molecule which hybridizes under stringent conditions to a nucleic acid molecule as defined in (i) above and which modulates CRLR function; and
iii) a polypeptide comprising a nucleic acid which is degenerate as a result of the genetic code to the nucleic acid sequence defined in (i) and (ii).

Preferably, the agent modulates the effect of a RAMP-3 protein which is defined above.

The agent of the present disclosure may be an antibody product selected from antibodies and antibody fragments; a protein; a polypeptide; a fusion protein; an aptamer; or a compound.

In a preferred embodiment of the invention said agent is an antagonist. Alternatively, said agent is an agonist.

According to a further aspect of the invention there is provided an agent that modulates the effect of a polypeptide on calcitonin receptor like receptor (CRLR) function wherein the polypeptide comprises an amino acid sequence as represented in FIG. 1, 2 or 3 (SEQ ID NO: 2, 4 or 6, respectively), or a variant polypeptide wherein said variant is modified by addition, deletion or substitution of at least one amino acid residue of the amino acid sequence presented in FIG. 1, 2 or 3 (SEQ ID NO: 2, 4 or 6, respectively), wherein said polypeptide modulates CRLR function, characterized in that said agent is for use as a pharmaceutical.

In addition, the present disclosure features polypeptide sequences having at least 75% identity with the polypeptide sequences as herein disclosed, or fragments and functionally equivalent polypeptides thereof. In one embodiment, the polypeptides have at least 85% identity, more preferably at least 90% identity, even more preferably at least 95% identity, still more preferably at least 97% identity, and most preferably at least 99% identity with the amino acid sequence illustrated herein.

The present disclosure includes a polypeptide comprising the amino acid sequence as shown in FIG. 4, 5 or 6 (SEQ ID NO: 8, 10 or 12, respectively), or a fragment or variant thereof wherein said variant is modified by addition, deletion or substitution of at least one amino acid residue of the amino acid sequence presented in FIG. 4, 5 or 6 (SEQ ID NO: 8, 10 or 12, respectively), wherein said polypeptide modulates CRLR function. Specifically, the agent modulates the effect of a RAMP protein as described above, on CRLR function.

As used herein "a fragment of a polypeptide comprising the amino acid sequence as shown in FIG. 4, 5 or 6" includes fragments that contain between 1 and 99 amino acids, for example between 1 and 50 amino acids such as between 1 and 30 amino acids or 10 and 30 amino acids. Preferably the fragments are N-terminal sequences of the RAMP proteins. For example the fragments may comprise 1-10, 10-20 or 20-30 amino acids at the N-terminus end of the amino acid sequences shown in FIG. 4, 5 or 6 (SEQ ID NO: 8, 10 or 12, respectively). Other fragments of the RAMP proteins may be, for example, 11, 12, 13, 14, 15, 16, 17, 18, 19 or 20 amino acid residues in length.

Included in the present disclosure are polypeptide fragments comprising one or more of the amino acid sequences shown in FIG. 7, 8 or 9 (SEQ ID NO: 14, 16, 18, 20, 22, 24, 26, 28, 30, 32, 34, 36, 37, 39, 41, 43, 45, 47, 49, 51, 53, 55, 57, 59, 61 or 63) or a variant polypeptide wherein said variant is modified by addition, deletion or substitution of at least one amino acid residue of an amino acid sequence presented in FIG. 7, 8 or 9 (SEQ ID NO: 14, 16, 18, 20, 22, 24, 26, 28, 30, 32, 34, 36, 37, 39, 41, 43, 45, 47, 49, 51, 53, 55, 57, 59, 61 or 63), wherein said polypeptide modulates CRLR function.

In an embodiment, the agent of the present disclosure is a polypeptide. The polypeptide may comprise the amino acid sequence as shown in FIG. 4, 5 or 6 (SEQ ID NO: 8, 10 or 12), or a fragment or variant thereof, wherein said polypeptide binds to a ligand of the RAMP proteins and/or a ligand of the CRLR.

The agent may be a polypeptide fragment that contains between 1 and 30 amino acids at the N-terminus end of the amino acid sequences shown in FIG. 4, 5 or 6 (SEQ ID NO: 8, 10 or 12), and optionally contains between 5 and 30 amino acids, and further optionally contains between about 10 and 30 amino acids at the N-terminus. In one embodiment, the fragment consists of an amino acid sequence selected from FIG. 7, 8 or 9 (SEQ ID NO: 14, 16, 18, 20, 22, 24, 26, 28, 30, 32, 34, 36, 37, 39, 41, 43, 45, 47, 49, 51, 53, 55, 57, 59, 61 or 63).

In one embodiment, in which the agent is not limited to being a polypeptide, the agent comprises a detectable marker. Preferably, the agent is provided with a marker including a conventional label or tag, for example a radioactive and/or fluorescent and/or epitope label or tag.

In an embodiment, the agent is an antibody product e.g. an antibody or an active binding part of an antibody. In an embodiment of the invention said antibody is a monoclonal antibody or active binding part thereof.

In a preferred embodiment of the invention said antibody is a chimeric antibody or a humanized antibody e.g. one produced by recombinant methods to contain the variable region of said antibody with an invariant or constant region of a human antibody.

As described in detail above, chimeric antibodies are recombinant antibodies in which all of the V-regions of a mouse or rat antibody are combined with human antibody C-regions. Humanized antibodies are recombinant hybrid antibodies which fuse the complementarity determining regions from a rodent antibody V-region with the framework regions from the human antibody V-regions. The complementarity determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen. Antibodies from non-human animals provoke an immune response to the foreign antibody and its removal from the circulation. Both chimeric and humanized antibodies have reduced antigenicity when injected to a human subject because there is a reduced amount of rodent (i.e. foreign) antibody within the recombinant hybrid antibody, while the human antibody regions do not illicit an immune response. This results in a weaker immune response and a decrease in the clearance of the antibody. This is clearly desirable when using therapeutic antibodies in the treatment of human diseases. Humanized antibodies are designed to have less "foreign" antibody regions and are therefore thought to be less immunogenic than chimeric antibodies. In an embodiment of the present invention, the agent of the present disclosure is a chimeric antibody. Optionally, the agent is a chimeric or humanized antibody or antibody fragment that binds to RAMP-3.

In an embodiment, the antibody product is an antibody fragment as described herein e.g. a single chain antibody, a single chain variable fragment (scFv), a domain antibody (dAB) or a nanobody, which binds to at least one of RAMP-1, RAMP-2 and RAMP-3 proteins as described herein e.g. in FIGS. 1, 2 and 3 (SEQ ID NO: 2, 4 and 6). Preferably, the antibody product modulates an effect of the RAMP protein on the CRLR protein. Such modulation may be for example inhibition of binding of the RAMP/CRLR heterodimer to a ligand. Whilst not being bound by theory, it is believed that the receptor formed by a RAMP/CRLR heterodimer acts as a receptor for specific ligands, e.g. adrenomedullin and CGRP. An agent of the present disclosure may act to interfere either with the association of the RAMP protein and the CRLR and/or with the binding of a ligand to the receptor. In one embodiment, the RAMP protein is RAMP-3. In a preferred embodiment of the invention said agent is an antibody fragment.

As indicated above, various fragments of immunoglobulin or antibodies are known in the art, i.e., Fab, Fab$_2$, F(ab')$_2$, Fv, Fc, Fd, scFvs, etc. A Fab fragment is a multimeric protein consisting of the immunologically active portions of an immunoglobulin heavy chain variable region and an immunoglobulin light chain variable region, covalently coupled together and capable of specifically binding to an antigen. Fab fragments are generated via proteolytic cleavage (with, for example, papain) of an intact immunoglobulin molecule. A Fab$_2$ fragment comprises two joined Fab fragments. When these two fragments are joined by the immunoglobulin hinge region, a F(ab')$_2$ fragment results. An Fv fragment is multimeric protein consisting of the immunologically active portions of an immunoglobulin heavy chain variable region and an immunoglobulin light chain variable region covalently coupled together and capable of specifically binding to an antigen. A fragment could also be a single chain polypeptide containing only one light chain variable region, or a fragment thereof that contains the three CDRs of the light chain variable region, without an associated heavy chain variable region, or a fragment thereof containing the three CDRs of the heavy chain variable region, without an associated light chain moiety; and multi specific antibodies formed from antibody fragments, this has for example been described in U.S. Pat. No. 6,248,516. Fv fragments or single region (domain) fragments are typically generated by expression in host cell lines of the relevant identified regions. These and other immunoglobulin or antibody fragments are within the scope of the invention and are described in standard immunology textbooks such as Paul, Fundamental Immunology or Janeway et al., Immunobiology (cited above). Molecular biology now allows direct synthesis (via expression in cells or chemically) of these fragments, as well as synthesis of combinations thereof.

It is possible to create single variable regions, so called single chain antibody variable region fragments (scFv's). If a hybridoma exists for a specific monoclonal antibody it is well within the knowledge of the skilled person to isolate scFv's from mRNA extracted from said hybridoma via RT PCR. Alternatively, phage display screening can be undertaken to identify clones expressing scFv's. Alternatively said fragments are "domain antibody fragments". Domain antibodies are the smallest binding part of an antibody (approximately 13 kDa). Examples of this technology are disclosed in U.S. Pat. Nos. 6,248,516, 6,291,158 and 6,127,197, and EP0368684 which are all incorporated by reference in their entirety.

In one embodiment of the invention the antibody fragment is a single chain antibody variable region fragment. A fragment of an antibody or immunoglobulin can also have bispecific function i.e. binding two different epitopes of two different antigens.

In one embodiment, the chimeric/humanized monoclonal antibody to the RAMP protein can be produced as a fusion polypeptide in an expression vector suitably adapted for transfection or transformation of prokaryotic or eukaryotic cells.

In a further preferred embodiment of the invention said antibodies are opsonic antibodies. Phagocytosis is mediated by macrophages and polymorphic leukocytes and involves the ingestion and digestion of micro-organisms, damaged or dead cells, cell debris, insoluble particles and activated clotting factors. Opsonins are agents which facilitate the phagocytosis of the above foreign bodies. Opsonic antibodies are therefore antibodies which provide the same function. Examples of opsonins are the Fc portion of an antibody or compliment C3.

In an embodiment of the invention said antibody, or antibody fragment has associated therewith, or crosslinked thereto, a therapeutic agent. Preferably said therapeutic agent is a chemotherapeutic agent. Preferably said therapeutic agent is selected from the group consisting of: cisplatin; carboplatin; cyclosphosphamide; melphalan; carmusline; methotrexate; 5-fluorouracil; cytarabine; mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate; and camptothecin. In one embodiment, the antibody product may be conjugated to e.g. a PEG molecule.

The binding of the agent e.g. to a RAMP protein for example RAMP-3 is optionally binding with an affinity of greater than $10^{-7}$ M, $10^{-18}$ M, $10^{-9}$ M, $10^{-10}$ M, $10^{-11}$ M or $10^{-12}$ M. The binding may be specific for the ligand or non-specific, although in some instances there is a degree of lower affinity non-specific binding to certain other ligands unrelated to RAMP-1, RAMP-2 or RAMP-3.

Thus, the agents of the invention may be, for example, an antibody or fragment thereof, e.g. a Fab fragment. However, also possible are aptamers, compounds, fusion proteins, proteins, peptides or combinations thereof as defined above. Particular antibodies and fragments are Fab fragments or scFv. Naturally within the scope of the agents of the invention are antibodies or fragments which are monoclonal, polyclonal, chimeric, human, or humanized. Other agents that bind to a RAMP protein, wherein the binding is described herein, are encompassed within the present invention.

Methods of antibody isolation are well known in the art. See, for example, Harlow and Lane (1988) Antibodies: A Laboratory Manual, Cold Spring Harbor Laboratory, New York. The method of isolation may depend on the immunoglobulin isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. Particularly, the agent of the invention is purified by using Protein G-Sepharose columns.

For most applications, it is generally preferable that the polypeptide e.g. an antibody is at least partially purified from other cellular constituents. Preferably, the polypeptide is at least about 50% pure as a weight percent of total protein. More preferably, the protein is at least about 50-75% pure. For clinical use, the polypeptide is preferably at least about 80% pure.

The agents of this invention can be made by any suitable procedure, including by recombinant methods or by chemical synthesis. Peptides which are produced may then be separated from each other by techniques known in the art, including but not limited to gel filtration chromatography, gel electrophoresis, and reverse-phase HPLC. Alternatively, agents of the invention can be chemically synthesized using information provided in this disclosure, in conjunction with standard methods of protein synthesis. A suitable method is the solid-phase Merrifield technique. Automated peptide synthesizers are commercially available, such as those manufactured by Applied Biosystems, Inc. (Foster City, Calif.).

Also included in the present invention is a method for the production of an antibody product e.g. an antibody or antibody fragment as described herein, and optionally of a chimeric antibody or a humanized antibody as defined herein comprising:

i) growing a cell transformed or transfected with a vector which comprises a nucleic acid molecule encoding the antibody or antibody fragment in conditions conducive to the manufacture of said antibody; and ii) purifying said antibody from said cell, or its growth environment.

In a yet further aspect of the invention there is provided a hybridoma cell line which produces a monoclonal antibody as hereinbefore described.

In a further aspect of the invention there is provided a method of producing monoclonal antibodies according to the invention using hybridoma cell lines according to the invention. The production of monoclonal antibodies using hybridoma cells is well-known in the art. The methods used to produce monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

In a further aspect of the invention there is provided a method for preparing a hybridoma cell-line producing monoclonal antibodies according to the invention comprising the steps of:

i) immunizing an immunocompetent mammal with an immunogen comprising at least one polypeptide having the amino acid sequence as represented in FIG. 4, 5 or 6 (SEQ ID NO: 8, 10 or 12), or a fragment or variant thereof as defined herein;

ii) fusing lymphocytes of the immunized immunocompetent mammal with myeloma cells to form hybridoma cells;

iii) screening monoclonal antibodies produced by the hybridoma cells of step (ii) for binding activity to the polypeptide of (i);

iv) culturing the hybridoma cells to proliferate and/or to secrete said monoclonal antibody; and v) recovering the monoclonal antibody from the culture supernatant.

In an embodiment of the invention the polypeptide in (i) comprises an amino acid sequence as shown in FIG. 7, 8 or 9 (SEQ ID NO: 14, 16, 18, 20, 22, 24, 26, 28, 30, 32, 34, 36, 37, 39, 41, 43, 45, 47, 49, 51, 53, 55, 57, 59, 61 or 63) or a variant polypeptide wherein said variant is modified by addition, deletion or substitution of at least one amino acid residue of an amino acid sequence presented in FIG. 7, 8 or 9 (SEQ ID NO: 14, 16, 18, 20, 22, 24, 26, 28, 30, 32, 34, 36, 37, 39, 41, 43, 45, 47, 49, 51, 53, 55, 57, 59, 61 or 63), wherein said polypeptide modulates CRLR function.

Preferably, the said immunocompetent mammal is a mouse. Alternatively, said immunocompetent mammal is a rat.

In an alternative embodiment of the invention said agent is a nucleic acid molecule. The nucleic acid may, for example, be an antisense nucleic acid; an aptamer; or a small interfering RNA.

In an embodiment of the invention said nucleic acid molecule can be a small interfering RNA. The small interfering RNA may be selected from the group consisting of sequences (1)-(5) below:

```
(1)
                                      (SEQ ID NO: 68)
          TGGCCCATCACCTCTTCATGA (2)
                                      (SEQ ID NO: 69)
          CTGGCTGCTCCTGGCCCATCA (3)
                                      (SEQ ID NO: 70)
          TCCTGGCCCATCACCTCTTCA (4)
                                      (SEQ ID NO: 71)
          CUAUGAGACAGCUGUCCAA (5)
                                      (SEQ ID NO: 72)
          GUUCUUCUCCAACUGCACC
```

A technique to specifically ablate gene function is through the introduction of double stranded RNA, also referred to as small inhibitory or interfering RNA (siRNA), into a cell which results in the destruction of mRNA complementary to the sequence included in the siRNA molecule. The siRNA molecule comprises two complementary strands of RNA (a sense strand and an antisense strand) annealed to each other to form a double stranded RNA molecule. The siRNA molecule is typically derived from exons of the gene which is to be ablated.

The mechanism of RNA interference is being elucidated. Many organisms respond to the presence of double stranded RNA by activating a cascade that leads to the formation of siRNA. The presence of double stranded RNA activates a protein complex comprising RNase III which processes the double stranded RNA into smaller fragments (siRNAs, approximately 21-29 nucleotides in length) which become part of a ribonucleoprotein complex. The siRNA acts as a guide for the RNase complex to cleave mRNA complementary to the antisense strand of the siRNA thereby resulting in destruction of the mRNA.

In another aspect, the invention provides an isolated nucleic acid comprising a nucleic acid sequence, which sequence encodes an agent described herein, which is an antibody, an antibody fragment, a fusion protein, a peptide or a protein.

The agents of the present invention, if comprising a peptide sequence, for example an antibody, a fusion protein, a peptide or a protein, may be encoded by a nucleic acid sequence. The present invention includes any nucleic acid sequence which encodes an agent as defined herein. The present invention also includes a nucleic acid sequence which encodes the agent of the invention but which differs from the wild-type nucleic acid as a result of the degeneracy of the genetic code.

The present invention also includes nucleic acids that share at least 90% homology with a nucleic acid sequence which encodes an agent of the present invention. In particular, the nucleic acid may have 90%, 91%, 92%, 93%, 94%, 95%, 96% 97%, 98% or 99% homology to a nucleic acid which encodes an antibody or fragment thereof of the present invention.

In one aspect of the invention, there is provided a nucleic acid molecule which hybridizes under stringent conditions to a nucleic acid molecule which encodes an agent of the present invention, when said agent is an antibody or fragment thereof or a fusion protein.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following have been found as exemplary for hybridization conditions but without limitation:

Very High Stringency (allows sequences that share at least 90% identity to hybridize)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (allows sequences that share at least 80% identity to hybridize)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (allows sequences that share at least 50% identity to hybridize)
  Hybridization: 6×SSC at RT to 55° C. for 16-20 hours
  Wash at least twice: 2×-3×SSC at RT to 55° C. for 20-30 minutes each.

In a further aspect, the invention provides an expression vector comprising a nucleic acid as described above and associated regulatory sequences necessary for expression of a protein or polypeptide in a host cell. Such regulatory sequences include promoters, termination sequences and enhancers, for example.

In another related aspect, the invention provides a host cell comprising a nucleic acid or a vector as described above. Such host cells are transfected or transformed so that they contain the nucleic acid or vector in such a way that they are effective in expressing the desired polypeptide/protein when cultured in appropriate media under the necessary growth conditions. The host cells to be used are not particularly circumscribed so as long as they can be transfected by a vector to be used and can express the DNA of the present invention. For example, bacteria such as *Escherichia coli*, yeast such as *Saccharomyces cerevisiae*, and an animal cell such as a COS cell, a CHO cell, etc. can be used. Examples of prokaryotic host cells appropriate for use with this invention include *E. coli*. Examples of eukaryotic host cells include avian, insect, plant, and animal cells such as COS7, HeLa, and CHO cells.

By cultivating a transformant or transfected cell, an agent of the invention for example a fusion protein, antibody or antibody fragment can be produced in a cell or a culture medium. Then, by collecting the produced antibody (or antibody fragment), the agent of the first aspect of the present invention can be obtained. The obtained antibody or protein can be isolated and purified by appropriately combining methods, for example centrifugation, ammonium sulfate fractionation, salting out, ultrafiltration, affinity chromatography, ion-exchange chromatography, or gel-filtration chromatography.

For example, the cells can be cultured in a suitable medium, and spent medium can be used as an antibody source. Optionally, matrix-coated channels or beads and cell cocultures may be included to enhance growth of antibody-producing cells. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal is optionally primed for ascites production by prior administration of a suitable composition, for example, Pristane. Antibodies of the invention may also be obtained by employing routine recombinant methods such as described in Sambrook et al. (1989) supra. For instance, nucleic acid sequences of the invention can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of antibodies of the invention may be produced separately, and then combined by disulfide bond rearrangement. Alternatively, vectors with separate polynucleotides encoding each chain of an antibody of the invention, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The fusion protein or antibody is thus produced in the host cell can be purified using standard techniques in the art.

According to a further aspect of the invention there is provided an assay for determining level of expression of a RAMP nucleic acid molecule e.g. having a sequence as shown in FIG. 1, 2 or 3 (SEQ ID NO: 1, 3 or 5), or a nucleic acid molecule that hybridizes to said nucleic acid molecule under stringent hybridization conditions and encodes a variant polypeptide comprising an amino acid sequence as represented in FIG. 1, 2 or 3 (SEQ ID NO: 1, 2 or 3), the method comprising the steps of:
i) contacting an isolated cell sample with a binding agent(s) that binds to a nucleic acid molecule that encodes a RAMP protein, and
ii) comparing the expression of said nucleic acid molecule in said sample with a standard sample.

The binding agent(s) may be selected from an oligonucleotide primer and an antibody that specifically binds said polypeptide as represented by the amino acid sequence in FIG. 1, 2 or 3 (SEQ ID NO: 2, 4 or 6). In one embodiment, the assay comprises a polymerase chain reaction.

In one aspect of the present invention, there is provided a diagnostic assay for the determination of cancer in a subject comprising the steps of:
i) providing an isolated cell sample;
ii) contacting the sample in (i) with a binding agent(s) that binds to a nucleic acid molecule that encodes a polypeptide comprising an amino acid sequence as represented in FIG. 1, 2 or 3 (SEQ ID NO: 2, 4 or 6), or a fragment or variant thereof as defined herein, or a nucleic acid molecule that hybridizes to said nucleic acid molecule under stringent hybridization conditions and encodes a variant polypeptide comprising an amino acid sequence as represented in FIG. 1, 2 or 3 (SEQ ID NO: 2, 4 or 6); and
iii) determining the expression of said nucleic acid molecule in said sample when compared to a normal matched control sample.

In a preferred embodiment of the invention said binding agent(s) is an oligonucleotide primer. Preferably said assay is a polymerase chain reaction. In an alternative preferred embodiment of the invention said binding agent is an antibody that specifically binds said polypeptide as represented by the amino acid sequence in FIG. 1, 2 or 3 (SEQ ID NO: 2, 4 or 6), or a polypeptide variant comprising an amino acid sequence that varies from a reference amino acid sequence by addition, deletion or substitution of at least one amino acid residue.

A further aspect of the present invention provides a method of screening for an agent that modulates the activity of a RAMP protein encoded by a nucleic acid molecule selected from the group consisting of:
a) a nucleic acid molecule consisting of a nucleic acid sequence as represented in FIG. 1, 2 or 3 (SEQ ID NO: 1, 3 or 5);
b) a nucleic acid molecule that hybridizes under stringent hybridization conditions to the nucleic acid molecule in (i) above and which modulates CRLR function;
said method comprising contacting a cell which expresses the RAMP protein on the cell surface with a test compound and determining the ability of the test compound to modulate the activity of the RAMP protein.

The present disclosure also provides a use of a RAMP protein in the identification of agents which modulate a CRLR function wherein the RAMP protein is selected from the group consisting of:
i) a polypeptide, or variant thereof, encoded by a nucleic acid molecule consisting of a nucleic acid sequence as represented by FIG. 1, 2 or 3 (SEQ ID NO: 1, 3 or 5);
ii) a polypeptide encoded by a nucleic acid molecule which hybridizes under stringent conditions to a nucleic acid molecule as defined in (i) above and which modulates CRLR function; and
iii) a polypeptide comprising a nucleic acid which is degenerate as a result of the genetic code to the nucleic acid sequence defined in (i) and (ii).

The present disclosure also provides a use of a CRLR in the identification of agents which modulate the interaction of CRLR with a polypeptide selected from the group consisting of:
i) a polypeptide, or variant thereof, encoded by a nucleic acid molecule consisting of a nucleic acid sequence as represented by FIG. 1, 2 or 3 (SEQ ID NO: 1, 3 or 5);
ii) a polypeptide encoded by a nucleic acid molecule which hybridizes under stringent conditions to a nucleic acid molecule as defined in (i) above and which modulates CRLR function; and
iii) a polypeptide comprising a nucleic acid which is degenerate as a result of the genetic code to the nucleic acid sequence defined in (i) and (ii).

According to a further aspect of the invention there is provided a kit comprising a binding agent specifically reactive with a nucleic acid molecule that encodes a polypeptide comprising an amino acid sequence as represented in FIG. 1, 2 or 3 (SEQ ID NO: 2, 4 or 6), or a fragment or variant thereof as defined herein, or an agent specifically reactive with a polypeptide comprising an amino acid sequence as represented in FIG. 1, 2 or 3 (SEQ ID NO: 2, 4 or 6), or a fragment or variant thereof as defined herein. In a preferred embodiment of the invention said kit further comprises an oligonucleotide or antibody specifically reactive with said nucleic acid molecule or said polypeptide.

Preferably said kit comprises a thermostable DNA polymerase and components required for conducting the amplification of nucleic acid. Preferably said kit includes a set of instructions for conducting said polymerase chain reaction and control nucleic acid.

In an alternative preferred embodiment of the invention said kit comprises an antibody specifically reactive with a polypeptide comprising an amino acid sequence as represented in FIG. 1, 2 or 3 (SEQ ID NO: 2, 4 or 6), or a fragment or variant thereof as defined herein. Preferably said kit comprises components required for conducting an immunoassay including, for example, a secondary antibody specifically reactive with a primary antibody that specifically binds said polypeptide(s) and enzyme reagents required to detect the binding of said secondary antibody with said primary antibody.

According to a further aspect of the invention there is provided a method to screen for an agent that modulates the activity of a polypeptide encoded by a nucleic acid molecule selected from the group consisting of:
a) a nucleic acid molecule consisting of a nucleic acid sequence as represented in FIG. 1, 2 or 3 (SEQ ID NO: 1, 3 or 5); and
b) a nucleic acid molecule that hybridizes under stringent hybridization conditions to the nucleic acid molecule in (a) above and which modulates CRLR function,
wherein the method comprises:
i) forming a preparation comprising a polypeptide, or sequence variant thereof, and at least one agent to be tested; and
ii) determining the activity of said agent with respect to the activity of said polypeptide.

The amino acid sequences represented in FIGS. 4 to 6 (SEQ ID NO: 8, 10 and 12), including FIGS. 7 to 9 (SEQ ID NO: 14, 16, 18, 20, 22, 24, 26, 28, 30, 32, 34, 36, 37, 39, 41, 43, 45, 47, 49, 51, 53, 55, 57, 59, 61 and 63) which correspond to RAMP extracellular domains (ECDs), can be used for the structure-based design of molecules which modulate CRLR function such as though the modulation of the association of RAMP to CRLR. Such "structure based design," is also known as "rational drug design." The RAMP ECDs can be three-dimensionally analyzed by, for example, X-ray crystallography, nuclear magnetic resonance or homology modeling, all of which are well-known methods. The use of structural information in molecular modeling software systems is also encompassed by the invention. Such computer-assisted modeling and drug design may utilize information such as chemical conformational analysis, electrostatic potential of the molecules, protein folding etc. One particular method of the invention may comprise analyzing the three-dimensional structure of the RAMP ECD for likely binding sites of targets, synthesizing a new molecule that incorporates a predictive reactive site, and assaying the new molecule as described above.

In a preferred method of the invention said agent is an antagonist. Agents identified by the screening method of the invention may include, antibodies, siRNA, aptamers, small organic molecules, (for example peptides, cyclic peptides), and dominant negative variants of the polypeptides herein disclosed.

As mentioned above, the invention also provides, in certain embodiments, "dominant negative" polypeptides derived from the polypeptides herein disclosed. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to another transcription factor or to a promoter site in the control region of a gene but does not increase gene transcription can reduce the effect of a normal transcription factor by occupying promoter binding sites without increasing transcription.

It will be apparent to one skilled in the art that modification to the amino acid sequence of peptides agents according to the present disclosure could enhance the binding and/or stability of the peptide with respect to its target sequence. In addition, modification of the peptide may also increase the in vivo stability of the peptide thereby reducing the effective amount of peptide necessary to inhibit the activity of the polypeptides herein disclosed. This would advantageously reduce undesirable side effects which may result in vivo. Modifications include, by example and not by way of limitation, acetylation and amidation. Alternatively or preferably, said modification includes the use of modified amino acids in the production of recombinant or synthetic forms of peptides. It will be apparent to one skilled in the art that modified amino acids include, for example, 4-hydroxyproline, 5-hydroxylysine, $N^6$-acetyllysine, $N^6$-methyllysine, $N^6,N^6$-dimethyllysine, $N^6,N^6,N^6$-trimethyllysine, cyclohexyalanine, D-amino acids, and ornithine. Other modifications include amino acids with a $C_2$, $C_3$ or $C_4$ alkyl R group optionally substituted by 1, 2 or 3 substituents selected from halo (eg F, Br, I), hydroxy or $C_1$-$C_4$ alkoxy. It will also be apparent to one skilled in the art that peptides which retain p53 binding activity could be modified by cyclisation. Cyclisation is known in the art, (see Scott et al., Chem. Biol. (2001), 8:801-815; Gellerman et al., J. Peptide Res. (2001), 57:277-291; Dutta et al., J. Peptide Res. (2000), 8:398-412; Ngoka and Gross, J. Amer. Soc. Mass. Spec. (1999), 10:360-363.

In a yet further aspect, the invention provides the use of a polypeptide in the identification of agents which modulate CRLR function wherein the polypeptide is selected from the group consisting of:
  i) a polypeptide, or variant thereof, encoded by a nucleic acid molecule consisting of a nucleic acid sequence as represented by FIG. 1, 2 or 3 (SEQ ID NO: 1, 3 or 5);
  ii) a polypeptide encoded by a nucleic acid molecule which hybridizes under stringent conditions to a nucleic acid molecule as defined in (i) above and which modulates CRLR function; and
  iii) a polypeptide comprising a nucleic acid which is degenerate as a result of the genetic code to the nucleic acid sequence defined in (i) and (ii).

A yet further aspect of the invention provides the use of a CRLR in the identification of agents which modulate the interaction of CRLR with a polypeptide selected from the group consisting of:
  i) a polypeptide, or variant thereof, encoded by a nucleic acid molecule consisting of a nucleic acid sequence as represented by FIG. 1, 2 or 3;
  ii) a polypeptide encoded by a nucleic acid molecule which hybridizes under stringent conditions to a nucleic acid molecule as defined in (i) above and which modulates CRLR function; and
  iii) a polypeptide comprising a nucleic acid which is degenerate as a result of the genetic code to the nucleic acid sequence defined in (i) and (ii).

Pharmaceutical Methods, Uses and Products

In other aspects the invention provides an agent as hereinbefore described for use as a pharmaceutical. In further aspects, there is provided a pharmaceutical formulation comprising an agent as hereinbefore described. The formulation may contain at least one additional pharmaceutically acceptable component, e.g. an excipient, diluent or carrier. Preferably, the formulation is intended for parenteral administration. In a particular embodiment, the formulation comprises an agent which is an antibody product, e.g. an antibody which binds to a RAMP-3 protein.

The extent of protection includes counterfeit or fraudulent products which contain or purport to contain an agent of the invention irrespective of whether they do in fact contain such an agent and irrespective of whether any such agent is contained in a therapeutically effective amount. Included in the scope of protection therefore are packages which include a description or instructions which indicate that the package contains a species or pharmaceutical formulation of the invention and a product which is or comprises, or purports to be or comprise, such a formulation or species.

According to a further aspect of the invention there is provided a pharmaceutical composition comprising an agent according to the invention. In a preferred embodiment, the agent is an antibody, particularly an antibody which binds to a RAMP-3 protein.

Encompassed in the present disclosure is a composition comprising a polypeptide comprising an amino acid sequence as represented in FIG. 4, 5 or 6 (SEQ ID NO: 8, 10 or 12), or a fragment thereof or a variant polypeptide wherein said variant is modified by addition, deletion or substitution of at least one amino acid residue of the amino acid sequence presented in FIG. 4, 5 or 6 (SEQ ID NO: 8, 10 or 12) and wherein said variant polypeptide modulates CRLR function.

As used herein "a fragment of a polypeptide comprising the amino acid sequence as shown in FIG. 4, 5 or 6" includes fragments that contain between 1 and 50 amino acids, for example between 1 and 30 amino acids such as between 10 and 30 amino acids. The fragment of a polypeptide comprising the amino acid sequence as shown in FIG. 4, 5 or 6 (SEQ ID NO: 8, 10 or 12), may comprise an amino acid sequence as shown in FIG. 7, 8 or 9 (SEQ ID NO: 14, 16, 18, 20, 22, 24, 26, 28, 30, 32, 34, 36, 37, 39, 41, 43, 45, 47, 49, 51, 53, 55, 57, 59, 61 and 63) or a variant polypeptide wherein said variant is modified by addition, deletion or substitution of at least one amino acid residue of an amino acid sequence presented in FIG. 7, 8 or 9 (SEQ ID NO: 14, 16, 18, 20, 22, 24, 26, 28, 30, 32, 34, 36, 37, 39, 41, 43, 45, 47, 49, 51, 53, 55, 57, 59, 61 and 63), wherein said polypeptide modulates CRLR function.

Also included in the present disclosure is a pharmaceutical composition comprising a nucleic acid molecule selected from the group consisting of:
i) a nucleic acid molecule comprising all or part of a nucleic acid sequence as represented by FIG. 4, 5 or 6 (SEQ ID NO: 7, 9 or 11); and
ii) a nucleic acid molecule that hybridizes under stringent hybridization conditions to the nucleic acid molecule in (i) above and which encodes a polypeptide wherein said polypeptide modulates CRLR function,
for use as a vaccine.

The present disclosure also envisages a composition comprising a nucleic acid sequence as represented by FIG. 4, 7, 8 or 9.

In a preferred aspect of the invention said composition includes an adjuvant and/or a carrier.

An adjuvant is a substance or procedure that augments specific immune responses to antigens by modulating the activity of immune cells. Examples of adjuvants include, by example only, Freunds adjuvant, muramyl dipeptides and liposomes. A carrier is an immunogenic molecule which, when bound to a second molecule, augments immune responses to the latter. Some antigens are not intrinsically immunogenic yet may be capable of generating antibody responses when associated with a foreign protein molecule such as keyhole-limpet haemocyanin or tetanus toxoid. Such antigens contain B-cell epitopes but no T cell epitopes. The protein moiety of such a conjugate (the "carrier" protein) provides T-cell epitopes which stimulate helper T-cells that in turn stimulate antigen-specific B-cells to differentiate into plasma cells and produce antibody against the antigen. Helper T-cells can also stimulate other immune cells such as cytotoxic T-cells, and a carrier can fulfill an analogous role in generating cell-mediated immunity as well as antibodies.

When administered, the pharmaceutical compositions and formulations of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents (for example, cisplatin; carboplatin; cyclosphosphamide; melphalan; carmusline; methotrexate; 5-fluorouracil; cytarabine; mercaptopurine; daunorubicin; doxorubicin; epirubicin; vinblastine; vincristine; dactinomycin; mitomycin C; taxol; L-asparaginase; G-CSF; etoposide; colchicine; derferoxamine mesylate; and camptothecin.

The compositions and formulations of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a one particular route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694-1712; incorporated herein by reference). Those of skill in the art can readily determine the various parameters and conditions for producing antibody aerosols without resort to undue experimentation.

The compositions and formulations of the invention are typically administered in effective amounts. An "effective amount" is that amount of a composition that alone, or together with further doses, produces the desired response. In the case of treating a particular disease, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein.

The doses of the agent administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of antibody are formulated and administered in doses between about 1 ng and about 1 mg, and preferably between 10 ng and 100 µg, according to any standard procedure in the art. Where nucleic acids or variants thereof are employed, doses of between 1 ng and 0.1 mg generally will be formulated and administered according to standard procedures. Other protocols for the administration of the compositions will be known to one of ordinary skill in the art, in which the dose amount, schedule of injections, sites of injections, mode of administration (e.g., intra-bone) and the like vary from the foregoing. Administration of the compositions to mammals other than humans, (e.g. for testing purposes or veterinary therapeutic purposes), is carried out under substantially the same conditions as described above. A subject, as used herein, is a mammal, preferably a human, and including a non-human primate, cow, horse, pig, sheep, goat, dog, cat or rodent.

When administered, the pharmaceutical preparations and formulations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Pharmaceutical compositions and formulations may comprise if desired, a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions and formulations may contain suitable buffering agents, including: acetic acid in a salt; citric acid in a salt; boric acid in a salt; and phosphoric acid in a salt. The pharmaceutical compositions and formulations also may contain, optionally, suitable preservatives, such as benzalkonium chloride, chlorobutanol, parabens, and thimero sal.

Compositions suitable for oral administration may be presented as discrete units, such as capsules, tablets, lozenges, each containing a predetermined amount of the active compound. Other compositions include suspensions in aqueous liquids or non-aqueous liquids such as syrup, elixir or an emulsion.

Compositions suitable for parenteral administration conveniently comprise a sterile aqueous or non-aqueous preparation of antibody or nucleic acids, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A further aspect of the invention provides an agent or composition as defined herein for use as a medicament. A preferred agent for use as a pharmaceutical is an antibody product e.g. an antibody or antibody fragment. A particular agent is an antibody product which binds to RAMP-3. Particularly, the antibody product binds to a human RAMP-3 protein.

In an aspect of the present invention, the agents of the present disclosure may be used to treat cancer. According to a further aspect of the invention there is provided a method to treat cancer in a subject comprising administering an effective amount of an agent according to the invention. In a preferred method of the invention said subject is human.

According to a further aspect of the invention there is provided a method to immunize an animal against cancer comprising administering an effective amount of a composition according to the invention. In a preferred method of the invention said animal is a human.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting, for example, lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary.

The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. Further types of cancer include leukemia, skin, intracranial and brain cancer.

The specific activities of AM in cancer pathobiology fall into five areas of action namely stimulation of cancer cell proliferation, indirect suppression of immune response, promotion of angiogenesis, encouragement of aggressive tumor phenotype, and apoptosis survival factor. Thus, an agent or composition according to the invention may be useful in the treatment, retardation and/or prevention of a cancerous condition through, for example, the inhibition of angiogenesis or cancer cell proliferation.

A pharmaceutical formulation comprising the agent of the present disclosure may be administered in combination, either sequentially or at a substantially similar time as a chemotherapeutic agent.

In one aspect of the present invention, the agent of the present invention, and/or a composition or formulation comprising the agent may be used to treat osteoporosis. Thus, according to an aspect of the invention there is provided a method to treat osteoporosis in a subject comprising administering an effective amount of an agent according to the invention. In a preferred method of the invention said subject is human.

In a further aspect of the present invention, the agent of the present invention, and/or a composition or formulation comprising the agent may be used to treat e.g. reduce a level of obesity. The agent may also be used for the manufacture of a medicament for the treatment of obesity. Thus, according to an aspect of the invention there is provided a method to treat obesity in a subject comprising administering an effective amount of an agent according to the invention. In a preferred method of the invention said subject is human.

Also included as an aspect of the present invention is a use of an agent as described herein for the manufacture of a medicament to treat or reduce angiopathy, e.g. angiopathy selected from diabetic angiopathy, microangiopathy and macroangiopathy. A method of treating angiopathy e.g. diabetic angiopathy comprising administering an agent of the present invention to a subject is included as an aspect of the present invention.

In a further aspect of the present invention, the agent of the present invention, and/or a composition or formulation comprising the agent may be used to treat an inflammatory disorder and/or inflammatory response. Thus, according to a further aspect of the invention there is provided a method to treat an inflammatory disorder in a subject comprising administering an effective amount of an agent according to the invention. In a preferred method of the invention said subject is human.

The inflammatory disorder may be selected from the group consisting of atherosclerosis, rheumatoid arthritis, osteoarthritis, gout, lupus erythematosus, scleroderma, Sjorgen's syndrome, poly- and dermatomyositis, vasculitis, tendonitis, synovitis, bacterial endocarditis, osteomyelitis, psoriasis, pneumonia, fibrosing alveolitis, chronic bronchitis, bronchiectasis, emphysema, silicosis, pneumoconiosis, tuberculosis, ulcerative colitis, Crohn's disease, chronic inflammatory demyelinating polyradiculoneuropathy, chronic inflammatory demyelinating polyneuropathy, multiple sclerosis, Guillan-Barre Syndrome and myasthemia gravis, mastitis, laminitis, laryngitis, chronic cholecystitis, Hashimoto's thyroiditis, and inflammatory breast disease. In an embodiment, the inflammatory disorder may be the result of tissue or organ rejection after transplantation. In a particular embodiment the inflammatory disorder is selected from the group consisting of atherosclerosis, rheumatoid arthritis, osteoarthritis, sepsis and polyarthritis.

In embodiments, the patient suffered, or is at risk or suspicion of having suffered, a disorder selected from the group consisting of thrombosis, myocardial infarction, stroke, transient ischemic attack, occlusive peripheral vascular disease, occlusion of a peripheral artery and complications thereof as a result of an inflammatory disease such as, for example, atherosclerosis.

The specification discloses also the local administration to an actual or suspected site of an atherosclerotic disorder of an agent according to the present invention. Such administration may be useful in the treatment of a patient suffering from, or suspected to be suffering from, an atherosclerotic disorder, e.g. an atherosclerotic plaque which may be ruptured. The administration may be via a catheter.

The agent of the present invention may be used to treat heart failure. Also provided is a use of an agent as described herein for the manufacture of a medicament to treat heart failure.

In a further aspect of the present invention, the agent of the present invention, and/or a composition or formulation comprising the agent may be used to treat sepsis. The agent may also be used for the manufacture of a medicament for the treatment of sepsis. Thus, according to an aspect of the invention there is provided a method to treat sepsis in a subject comprising administering an effective amount of an agent according to the invention. In a preferred method of the invention said subject is human.

In an embodiment of the present invention, the agent may be useful in treating a wound, that is to say useful in aiding wound healing. A further aspect of the invention provides a method to treat a wound in a subject comprising administering an effective amount of an agent according to the invention. In a preferred method of the invention said subject is human. Also provided is a use of an agent according to the invention for the manufacture of a medicament to treat a wound.

As used herein, treatment of a "wound" includes, inter alia, treatment of ulcers and lesions for example, cutaneous wounds as such cuts or burns, and conditions associated therewith.

As used herein, "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, diminishment of any direct or indirect pathological consequences of the disease, lowering the rate of disease progression, amelioration or palliation of the disease state, and remission or improved prognosis. The term, "treatment" as used herein is intended to include the treatment and prevention of the indicated conditions/disorders There is further provided a package or kit of parts comprising:

(1) an agent described herein; together with (2) instructions to use the agent in a method described herein.

The package defined herein may comprise more than one dosage unit, in order to provide for repeat dosing. If more than one dosage unit is present, such units may be the same, or may be different in terms of the dose of active agent composition and/or physical form.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

An embodiment of the invention will now be described by way of example only and with reference to the following Figures and Materials and Methods.

FIG. 1 shows the DNA sequence of RAMP 1 (top) (SEQ ID NO: 1); and the amino acid sequence encoded by the DNA sequence (bottom) (SEQ ID NO: 2).

FIG. 2 shows the DNA sequence of RAMP 2 (top) (SEQ ID NO: 3); and the amino acid sequence encoded by the DNA sequence (bottom) (SEQ ID NO: 4).

FIG. 3 shows the DNA sequence of RAMP 3 (top) (SEQ ID NO: 5); and the amino acid sequence encoded by the DNA sequence (bottom) (SEQ ID NO: 6).

FIG. 4 shows the DNA sequence corresponding to a region of the extracellular domain (ECD) of RAMP 1 (top)

(SEQ ID NO: 7); and the amino acid sequence encoded by the DNA sequence (bottom) (SEQ ID NO: 8).

FIG. 5 shows the DNA sequence corresponding to a region of the extracellular domain (ECD) of RAMP 2 (top) (SEQ ID NO: 9); and the amino acid sequence encoded by the DNA sequence (bottom) (SEQ ID NO: 10).

FIG. 6 shows the DNA sequence corresponding to a region of the extracellular domain (ECD) of RAMP 3 (top) (SEQ ID NO: 11); and the amino acid sequence encoded by the DNA sequence (bottom) (SEQ ID NO: 12).

FIGS. 7A-H show DNA sequences corresponding to truncated regions of the N-terminal end of the extracellular domain (ECD) of RAMP 1 (top) (SEQ ID NO: 13, 14, 15, 16, 17, 18, 19, and 20); and the amino acid sequences encoded by the DNA sequences (bottom) (SEQ ID NO: 21, 22, 23, 24, 25, 26, 27 and 28): Fragment lengths are shown in bold.

FIGS. 8A-J show DNA sequences corresponding to truncated regions of the N-terminal end of the extracellular domain (ECD) of RAMP 2 (top) (SEQ ID NO: 29, 30, 31, 32, 33, 34, 35, 36 and 37); and the amino acid sequences encoded by the DNA sequences (bottom) (SEQ ID NO: 38, 39, 40, 41, 42, 43, 44, 45, 46 and 47): Fragment lengths are shown in bold.

FIGS. 9A-H show DNA sequences corresponding to truncated regions of the N-terminal end of the extracellular domain (ECD) of RAMP 3 (top) (SEQ ID NO: 48, 49, 50, 51, 52, 53, 54, and 55); and the amino acid sequences encoded by the DNA sequences (bottom) (SEQ ID NO: 56, 57, 58, 59, 60, 61, 62 and 63). Fragment lengths are shown in bold.

FIG. 10 shows the DNA (top) (SEQ ID NO: 64) and amino acid (bottom) sequence of CRLR (SEQ ID NO: 65).

Figure 11:
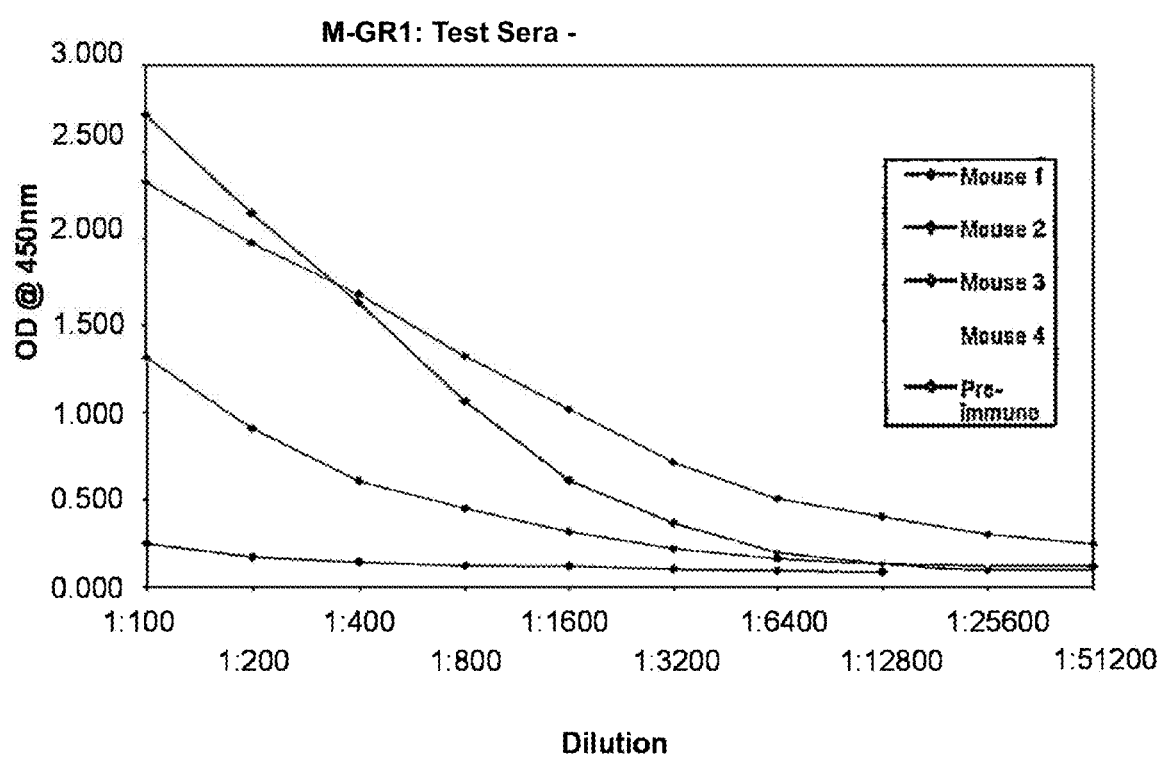

FIG. 11 shows ELISA data for mouse anti-RAMP 3 polyclonal antibodies.

Figure 12:
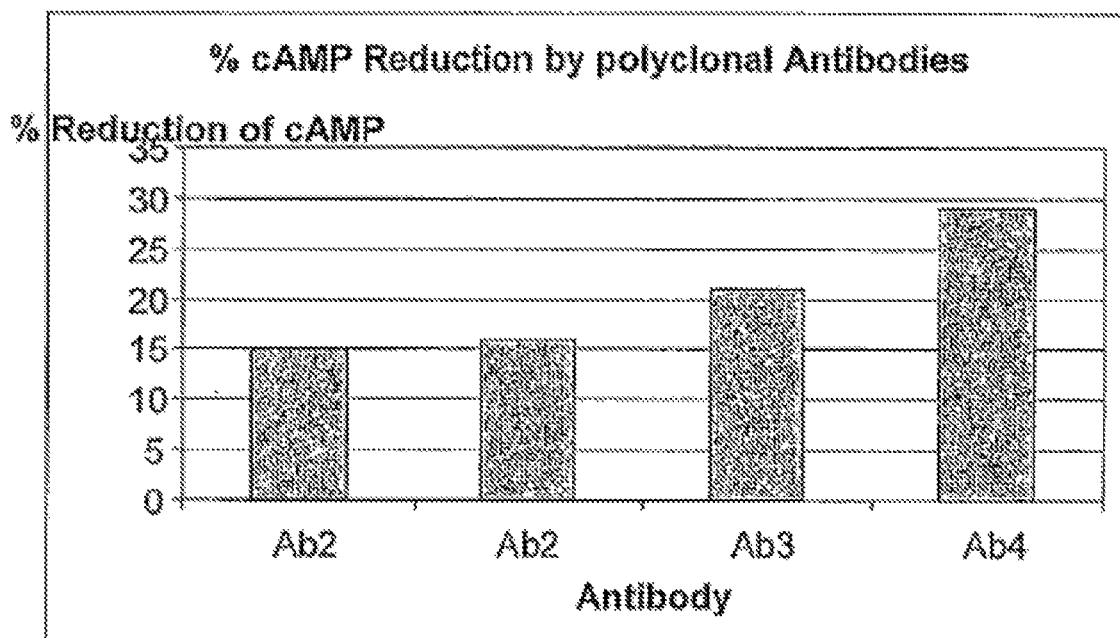

FIG. 12: Polyclonal anti-RAMP-3 antibodies were tested for their ability to regulate the effect of adrenomedullin to increase cyclic AMP in human MG63 osteosarcoma cells. All antibodies reduced the effect of adrenomedullin.

Figure 13:
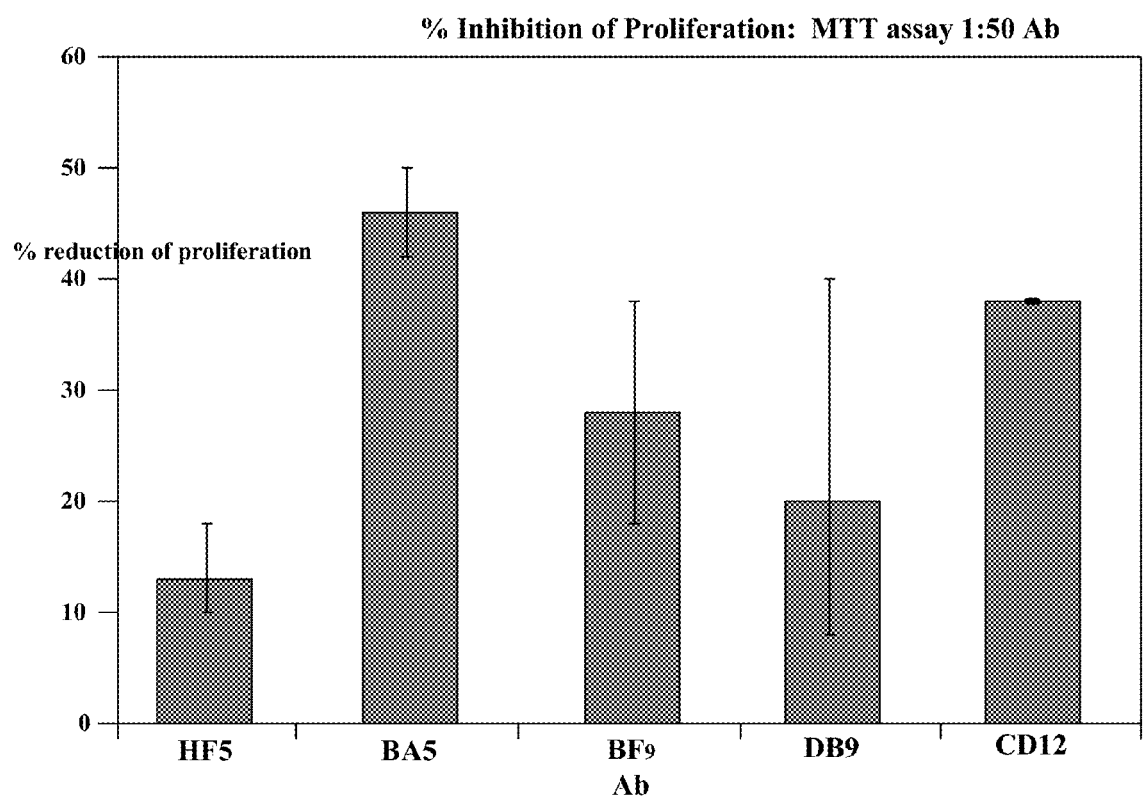

FIG. 13: Monoclonal anti-RAMP-3 antibodies were tested for their ability to induce inhibition of proliferation (based on the MTT assay of mitochondrial succinate dehydrogense, which maps to proliferation). The concentration of 1:50 equates to about 5 ng per well final concentration.

Figure 14:
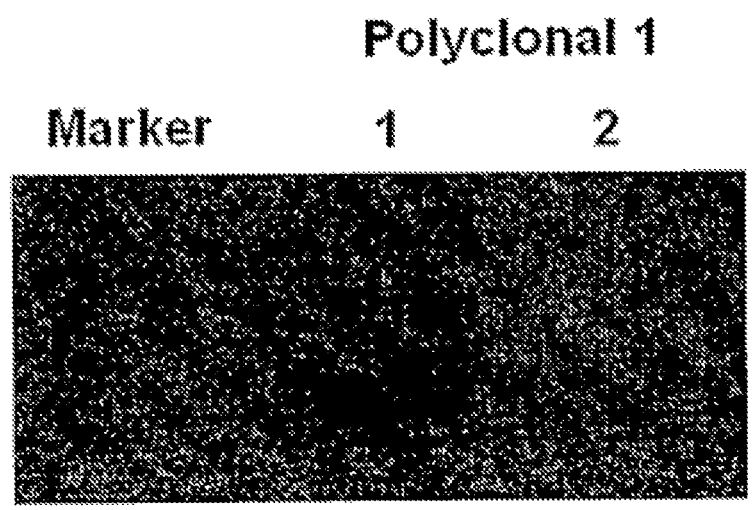

FIG. 14 is a Western Blot of polyclonal antibodies from mouse 1.

Figure 15:
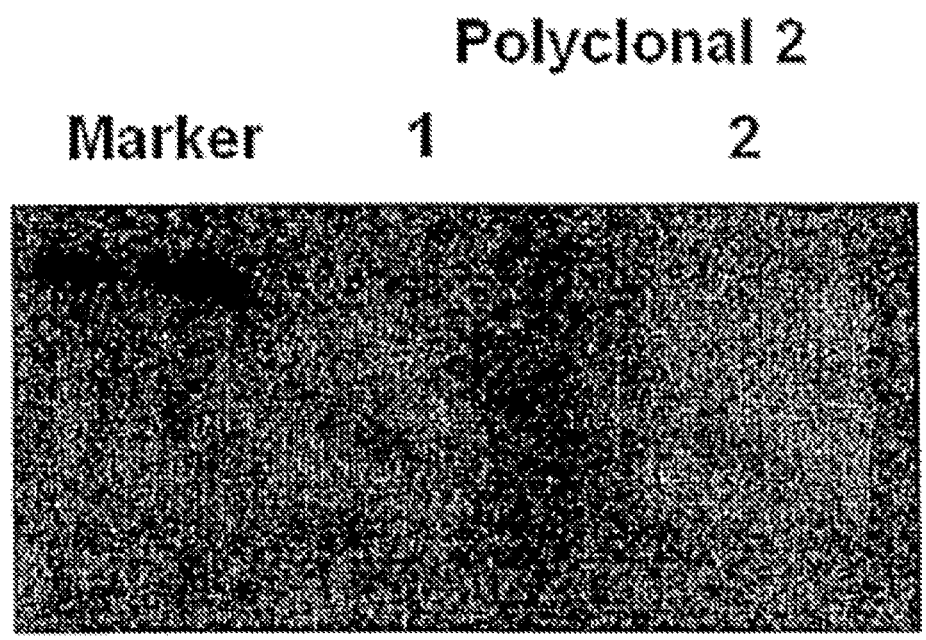

FIG. 15 is a Western Blot of polyclonal antibodies from mouse 2.

Figure 16:
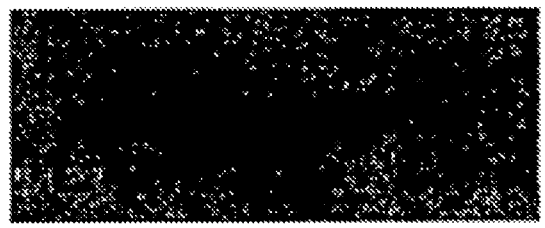

FIG. 16 is a Western Blot of polyclonal antibodies from mouse 3.

DETAILED DESCRIPTION

Examples

Generation of the RAMP Extra Cellular Domain (ECD) Protein

The ECD regions of the RAMP were generated using a high fidelity PCR reaction using KOD Hot Start DNA Polymerase kit from Novagen Toyobo. The template DNA was obtained from a purchased sample of human brain cDNA (Ambion).

For each 50 µl reaction, the following were placed in a 0.5 ml PCR tube at room temperature or on ice:

| | |
|---|---|
| 27.5 µl | PCR Grade H$_2$O |
| 2.5 µl | DMSO |
| 5 µl | 10X PCR Buffer for KOD Hot Start DNA Polymerase |
| 5 µl | dNTPs (final concentration 0.2 mM) |
| 2 µl | MgSO$_4$ (final concentration 1 mM) |
| 1 µl | Template DNA |
| 3 µl | 5' primer (5 pmol/µl, final concentration 0.3 µM) |
| 3 µl | 3' primer (5 pmol/µl, final concentration 0.3 µM) |
| 1 µl | KOD Hot Start DNA Polymerase (1 U/µl) |
| 50 µl | Total volume |

This reaction was carried out twice: the first reaction was carried out to isolate a region larger than the whole RAMP ECD using the following primers:

```
RAMP1
Forward
                                       (SEQ ID NO: 73)
CGAGCGGACTCGACTCGGCAC Reverse
                                       (SEQ ID NO: 74)
CTTCCTAGGGTGGCGGTGGCC RAMP2
Forward
                                       (SEQ ID NO: 75)
GTC CGC CTC CTC CTT CT GCT Reverse
                                       (SEQ ID NO: 76)
AAG TGG AGT AAC ATG GTT ATT GT RAMP3
Forward
                                       (SEQ ID NO: 77)
AGC CAT GGA GAC TGG AGC GCT GC Reverse
                                       (SEQ ID NO: 78)
GTG GCC CAG TAG CTG GAG ATT GGC
```

The reaction is purified using the QIAGEN QiAquick PCR purification kit standard protocol using a bench top centrifuge.

The second PCR reaction uses the products from the reaction above, using the primers below. These primers have had EcoR1 and BamH1 restriction sites incorporated into them:

```
RAMP1
Forward
                                       (SEQ ID NO: 79)
GCGAATTCCTGCCAGACCACCAG Reverse
                                       (SEQ ID NO: 80)
GTGGATCCTACCGGGCCCGGGACA RAMP2
Forward
                                       (SEQ ID NO: 81)
GCG AAT TCA ATC CCC ACG AGG CCC TGG CTC AGC C Reverse
                                       (SEQ ID NO: 82)
CAG GAT CCTACA AGA GTG ATG AGG AAG GGG ATG RAMP3
Forward
                                       (SEQ ID NO: 83)
CAG AATT TCC AGA GCA GGC CGC TGC AAC CAG ACA G
```

Reverse
(SEQ ID NO: 84)
GTG GAT CCC ACC ACC AGG CCA GCC ATG GCG ACA GT

The samples from this reaction are purified using QIAGEN QiAquick PCR purification kit using a bench top centrifuge.

To initially screen the products for size, they are run on a 1.5% agarose gel containing 1.5% ethidium bromide run at 200V for 30 minutes. The products are compared against a standard marker available from Sigma.

Genomic sequencing of the product is performed to test the product conclusively. The ECD protein from this point onwards will be referred to as "the insert" unless stated otherwise.

Preparation of the Insert and Vector

1. Restriction (These quantities are based on DNA concentration of 1 µg)

The restriction reaction was performed on both the insert and Vector (pGEX-6P1) using the following protocol.

| | |
|---|---|
| 1 µl | DNA |
| 2 µl | 10xBufferE |
| 2 µl | 10XBSA |
| 1 µl | BamH-1 |
| 1 µl | EcoR-1 |
| 13 µl | DNase free H₂O |
| 20 µl | Total Volume |

This reaction is either incubated at 37° C. for 1 hr or 16° C. overnight. The samples from this reaction were purified using QIAGEN QiAquick PCR purification kit using a bench top centrifuge standard protocol.

2. Vector Dephosphorylation

These quantities are based on DNA concentration of 1 µg

| | |
|---|---|
| 1 µl | DNA |
| 1 µl | 10xAntarctic Phosphatase Reaction Buffer |
| 1 µl | Antarctic Phosphatase |
| 7 µl | DNase free H₂O |
| 10 µl | Total Volume |

Incubate at 37° C. for 1 hr.

3. Ligation (Plasmid+Insert)

These quantities are based on DNA concentration of 1 µg

| | |
|---|---|
| 1 µl | Vector |
| 1 µl | Insert DNA |
| 5 µl | x2 Ligation Buffer |
| 1 µl | T4 Ligase |
| 2 µl | DNase free H₂O |
| 10 µl | Total Volume |

Incubate at 16° C. overnight.

Transformation

The total volume from the ligation reaction was used in the below steps:

| | |
|---|---|
| 10 µl | DNA |
| 10 µl | X10 Transformation Buffer |
| 100 µl | *E-Coli* (TOP10) competent cells |
| 70 µl | DNase free H₂O |
| 200 µl | Total Volume |

X10 Transformation Buffer. (300 mM MgCl₂, 100 mM CaCl₂)

| | |
|---|---|
| 6.5 ml | Distilled water |
| 0.5 ml | 2M CaCl₂ |
| 3.0 ml | 1M MgCl₂ |
| 10 ml | Total Volume |

1. Place on ice for 20 minutes.
2. Place at room temperature 10 minutes
3. Add 1 ml of LB Broth Base (LENNOX L Broth Base)
4. Incubate at 37° C. for 1 hour.
5. Spread Sample over LB Agar plates containing 10 µg/ml Ampicillin.
6. Incubate at 37° C. overnight.

Culture

Colonies from plates are picked and placed into 5 ml LB Broth Base (LENNOX L Broth Base) containing 10 µg/ml Ampicillin, then placed in shaking incubator overnight at 37° C.

The culture is cleaned up using QIAprep Spin Miniprpep Kit (Qiagen) standard protocol using table top centrifuge. To ensure that transformation has occurred efficiently, genomic sequencing is carried out on a sample of the plasmid.

Protein Expression

The following protocol was followed for protein expression:

Transformation

| | |
|---|---|
| 1 µl | DNA (1~10 ng) |
| 10 µl | X10 Transformation Buffer |
| 100 µl | *E-Coli* (BL21) Competent cells |
| 89 µl | Distilled H₂O |
| 200 µl | Total Volume |

1. Place on ice for 20 minutes.
2. Place at room temperature 10 minutes
3. Add 1ml of LB Broth Base (LENNOX L Broth Base)
4. Incubate at 37° C. for 1 hour.
5. Spread Sample over LB Agar plates containing 10 µg/ml Ampicillin.

Incubated at 37° C. overnight.

The following protocol was used to culture the cells:

Culture

Pick colonies and place into 5 ml 2×YTA medium (10 µg/ml Ampicillin). 2×YTA Medium

| | |
|---|---|
| 16 g | Tryptone |
| 10 g | Yeast Extract |
| 5 g | NaCl |
| 900 ml | Distilled H₂O |

The pH7 is adjusted with NaOH. The total volume is adjusted to 1 L with distilled H₂O and sterilised by autoclaving. Ampicillin concentration of 10 µg/ml is added. The following protocol steps were followed:

1. Incubate at 37° C. in shaking incubator for 2 hours.
2. Add 150 µl 100 mM IPTG to the culture.
3. Incubate at 37° C. in shaking incubator for an addition 4-8 hours Protein Extraction The protein was extracted using the Bug Buster Protein Extraction Reagent (Novagen) using the standard protocols. This includes the addition stage of the addition of protease inhibitors. Both the soluble and insoluble fraction were kept and analyzed.

Conformation of Protein

This process is carried out using Western blotting, using Anti-GST antibody (Amersham Biosciences). The Western blots are carried out as stated in the Anti-GST antibody protocol.

Protein Purification

Large scale protein production is performed at 2 L cultures.

The protein is purified using the Glutathione S-transferase (GST) gene fusion system. GST occurs naturally at a $M_r$ 26,000 that can be expressed in E. coli with full enzymatic activity. GST fusion proteins are purified from bacterial lysates by affinity chromatography using immobilized glutathione. GST fusion proteins are captured by the affinity medium, and impurities are removed by washing. Fusion proteins are eluted under mild, non-denaturing conditions using reduced glutathione. GSTrap HP 5 ml columns (Amersham Biosciences) are used to purify the samples.

The purification process preserves protein antigenicity and function. Once eluted, the GST can be cleaved from the protein using site specific protease. This process will be carried out as stated in the GST gene fusion system hand book (Amersham Biosciences).

The above purification methods are also supplemented by a process of fractionation purification. Once the protein has been purified a conjugated form of the peptide is sent to be used in the generation of monoclonal antibodies. The remaining protein solution is treated with specific proteases to remove the GST tag.

Functional Tests ECD Protein

MG63 human osteoblast-like cells will be manipulated by siRNA to produce various RAMP cell phenotypes:
RAMP 1, 2 and 3 negative cells, CRLR positive cells (Line 1).
RAMP 2 and 3 negative cells, RAMP 1 and CRLR positive cells (Line 2).
RAMP 1 and 3 negative cells, RAMP 2 and CRLR positive cells (Line 3).
RAMP 1 and 2 negative cells, RAMP 3 and CRLR positive cells (Line 4).

```
RAMP1:
(Qiagen)
T G G C C C A T C A C C T C T T C A T G A (Qiagen)
C T G G C T G C T C C T G G C C C A T C A (Qiagen)
T C C T G G C C C A T C A C C T C T T C A
```

Due to the nature of the RAMP1 gene no one siRNA appears to be conclusively so several siRNA will be tested.

```
RAMP2:
(MWG)
CUAUGAGACAGCUGUCCAA
```

```
RAMP3:
(MWG)
GUUCUUCUCCAACUGCACC
```

The transfection of the siRNA will be carried out using the HiPerFect Transfection Kit (Qiagen) standard protocol as stated in the handbook.

Function Test 1

The first experiment will be to determine whether the ECD fragments are able to engender a RAMP phenotype on a RAMP naïve cell (Line 1)

Culture (50 µl volumes) in solid, black 96-well microplates (Corning) with cell concentrations of between $10^4$ and $10^6$ cells/ml Incubate at 37° C. overnight (5% $CO_2$ AND 95% humidity) aspirate the cell culture media.

Add 50 µl volume of ECD or agonist made up in PBS and exposed for 5 minutes.

Dose responses for ECD will be carried out to determine effective concentrations.

Dose responses for agonist (adrenomedullin AM, calcitonin gene related peptide CGRP) will also be carried out to determine whether a response can be elicited from the agonist.

On addition of both ECD and agonist individually cAMP response will be measured using cAMP Fluorescence Polarization (FP) Biotrak Immunoassay (Amersham Biosciences)

A dose of ECD and the corresponding agonist will be applied in combination (e.g. RAMP1 and CGRP) and second messenger will be measured (as above).

Function Test 2

This experiment will determine the ability of RAMP ECD to redefine a predefined RAMP cell phenotype e.g. convert a RAMP1 type cell to a RAMP2 type cell (Lines 2, 3 and 4)

A dose response curve will be carried out using the ligand associated with the RAMP. Second messenger responses will be measured. $EC_{50}$ concentration determined.

ECD dose response curve will be created all in the presence of the $EC_{50}$ concentration of the ligand in question. Second messenger response will be measured.

Should a reduction in second messenger be seen in response to that ligand, the corresponding ligand to the ECD will be applied and second messenger response will be measured.

These two initial experiments will help determine whether ECD regions have biological activity Antibody Generation.

The ECD peptides were expressed as described above and then purified. Antibodies were generated using the following protocol.

Mouse and Rat Immunization Protocol

The following immunization protocol was followed to raise antibodies against the extracellular domain of RAMP-3:

Pre-immune serum was taken from the mice prior to immunisation. Four mice were injected with a peptide corresponding to an extracellular domain of RAMP-3:

```
          10         20         30         40         50         60
     GCPRAGGCNE TGMLERLPLC GKAFADMMGK VDVWKWCNLS 70         80         90
     EFIVYYESFT NCTEMEANVV GCYWPNPLAQ GFITGIHRQF

99
     FSNCTVDRVH LEDPPDEVL
     (see also FIG. 6; SEQ ID NO: 12)
```

Injections were boosted with 4 further injections, at approximately monthly intervals. Sample bleeds from the mice were taken to isolate serum containing polyclonal antibodies.

The adjuvant used was Freunds (complete for the first injection, followed by incomplete for the rest of the course.)

Antigen and adjuvant are normally mixed on site just prior to injection. Ideally, enough antigen should be supplied at the start to complete the course, although this may not always be necessary. Up to 20% of the antigen may be lost at the time of mixing, which should be allowed for. The total volume that can be injected into rodents is 0.2 ml (and preferably no more than 0.1 ml for mice). Half of this will be antigen and half adjuvant therefore the antigen should be of sufficient concentration to provide the required number of milligrams in a maximum of 0.1 ml or 0.05 ml injected.

Rabbit Immunization Protocol

Pre-immune serum can be taken if required. Rabbits are normally injected at four week intervals. No less than two weeks and no more than eight weeks can elapse between injections. A maximum of five injections can be given altogether, and the procedure should ideally be complete within six months. A blood sample is normally taken after the third injection to assess immune status.

At the end of the procedure, the rabbits are normally sacrificed and bled out for serum. Alternatively, the animals can be bled to the maximum allowed and then released. The commonest adjuvant used is Freunds (complete for the first injection, followed by incomplete for the rest of the course). If preferred, a less irritating adjuvant (or none at all) can be used instead.

Antigen and adjuvant are normally mixed on site just prior to injection. Ideally enough antigens for at least four injections (and preferably five) should be supplied at the beginning of the procedure. Up to 20% of the antigen may be lost at the time of mixing, which should be allowed for. Typically a total volume of no more than 0.5 ml is injected into each animal on each occasion. Half of this will be antigen and half adjuvant. Therefore the antigen should be of sufficient concentration to provide the required number of milligrams in a maximum of 0.25 ml injected.

Western Blot Protocol

Western blots of the antibodies were used to probe blots of the original ECD peptide of FIG. 6 run in duplicate lanes with a size marker. Antibody 1 and 2 show clear binding to the protein bands at the expected size of 14 KDa. Antibody 3 shows very strong binding at the same size, while AB4 was not detectable in this experiment.

Protein preparation (Based on the protein extraction yield (as determined by Bradford Assay)).

The protein used was the RAMP ECD. 10 ul of Laemlli buffer was added to a micro tube. DTT was added (5% of total volume). A protein sample volume that contained 100-150 μg of protein to the tube was added with the other reagents. The micro tubes were heated at 70 degrees Celsius for 2 minutes, and then placed on ice.

Separation

A 15% Acrylamide gels 15% were used.

A running buffer was produced according to the following recipe:

Running Buffer:
Tris Base 60.55
glycine 288.27 g
SDS 20 gdH2O—complete up to 2 liters The gels were placed into electrode house place in tank and submerged with running buffer. The gels were then allowed to stand for 20 minutes. The samples were loaded in lanes and the gel run at 200 V for 40 minutes.

Transfer

Filter paper (typical chromatography paper) was in approximately 7×20 cm pieces and PVDF membrane was cut to 7×20 cm. The PVDF membrane was pre-wet using 100% methanol for 10 seconds and immersed in dH2O. The filter pads were soaked in transfer buffer which comprised the following:

Transfer Buffer
Trisbase 12.11 g
Glycine 57.65 g
Methanol—100 ml
dH2O—complete up to 4 liters The membrane sandwich was assembled according to the kit instructions. The sandwich was placed into the transfer assembly and the transfer tank was filed with transfer buffer. The cooling block was removed from storage at −20 degrees Celsius, and placed into the transfer apparatus. The gel was run at 100 V for 1 hour.

Probing the PDVF

The blots were blocked in 5% milk for 1 hour. The anti-RAMP-3 ECD antibodies were diluted 1:00 5% milk and incubated overnight with the blot before being washed in PBS 5%

Tween-20 3×5 min. Secondary antibody HRP Anti-Mouse diluted 1:1000 in 5% milk was added and incubated for 1 hour. A further washing in PBS 5% Tween-20 3×5 min followed by washing with water 3×5 min was carried out.

To image the blots, ECL solution was added to the blots make sure through soaking both sides. (ECL available from Santa Cruz). The blots were revealed using photographic film from Amersham Biosciences.

Antibody Blocking Potential.

To test the ability of the antibodies to bind to RAMP, assays were carried out to determine the antibodies' blocking potential:

Human MG63 osteosarcoma cells were treated with 10 pmol of AM and the cAMP response measured (method as stated above e.g. using cAMP Fluorescence Polarization (FP) Biotrak Immunoassay (Amersham Biosciences)). (If RAMP-1 agents are being tested, this assay can also be carried out using CGRP as a ligand to test the agent's blocking ability.)

The cells were pre-treated with the antibody for 1 hr

An $EC_{50}$ dose of AM was applied (10 pmol) was applied and cAMP response was measured.

The polyclonals were used to test their ability to regulate the effect of adrenomedullin to increase cyclic AMP in human MG63 osteosarcoma cells. All polyclonal antibodies tested reduced the effect of adrenomedullin on cAMP production. The results shown in FIG. 12 indicate that the polyclonal antibodies raised against RAMP-3 inhibited cAMP production of the MG63 cells by at least 15%.

Monoclonal Antibody Production

Although antibody 4 gave highest inhibition, because it was not seen on the western blot and because the binding curve of AB3 was much stronger at low dilutions, monoclonal antibodies were produced using the 3$^{rd}$ mouse. The methods used to produce the monoclonal antibodies are disclosed by Kohler and Milstein in Nature 256, 495-497 (1975) and also by Donillard and Hoffman, "Basic Facts about Hybridomas" in Compendium of Immunology V.II ed. by Schwartz, 1981, which are incorporated by reference.

Screening of the clones was carried out and from approximately 1000 clones, 576 were selected on the basis of not binding to the GST tag on the peptide. Of these clones, ELISA data was obtained and the best 5 were selected for further work.

Antibody Function

The five monoclonal antibodies were tested for their effect on AM function. The proliferation/survival of SW-13 cells was determined using the MTT assay (see www.lgcpromo-chem-atcc.com for details on the assay). The following protocol was used:

Culture Media
DMEM
20% FCS
5% antibiotic/mitotic
5% sodium pyruvate

The cells were plated at 1×10$^6$ in 96 well plates using 50 ul of media in each well. SW-13 cells (human adrenal cortical adenocarcinoma cell line) were used in this method. The antibodies are applied in a 1:50 dilution in each well and incubated over night.

10 ul MTT Reagent was added to each well and then incubated for between about 2 to 4 hours until purple precipitate is visible. 100 ul Detergent Reagent was added to lyse the cells and solubilize the precipitate and then left at room temperature in the dark for 2 hours. The absorbance was recorded at 570 nm using an ELISA plate reader.

Each monoclonal antibody produced induced inhibition of proliferation ranging from 12-45% see FIG. 13. (The concentration of 1:50 equates to about 5 nanogrammes per well final concentration).

The invention claimed is:

1. An antibody or an antigen-binding fragment thereof that binds to the peptide of SEQ ID NO: 67.

2. An antibody or antigen-binding fragment thereof according to claim 1, wherein the antibody or antigen-binding fragment thereof is a monoclonal antibody or an antigen-binding fragment thereof.

3. An antibody or antigen-binding fragment thereof according to claim 1, wherein the antibody or antigen-binding fragment thereof is a scFV, Fab, Fab$_2$, F(ab')$_2$, Fv or dAB.

4. An agent according to claim 1, wherein the antibody or antigen-binding fragment thereof is a chimeric antibody, humanized antibody, or an antigen-binding fragment of either thereof.

5. A pharmaceutical formulation comprising an antibody or antigen-binding fragment thereof according to claim 1 and a pharmaceutically acceptable carrier, diluent or excipient.

6. The pharmaceutical formulation of claim 5, wherein the pharmaceutical formulation further comprises a chemotherapeutic agent.

7. The antibody of claim 1.

8. The antibody or an antigen-binding fragment thereof of claim 1, wherein the antibody or antigen-binding fragment thereof binds to the extracellular domain of RAMP-3 with an affinity of greater than $10^{-8}$ M.

* * * * *